United States Patent [19]
Bito et al.

[11] Patent Number: 5,649,937
[45] Date of Patent: Jul. 22, 1997

[54] TISSUE-FIXING SURGICAL DEVICE, AND METHOD OF FIXING TISSUES

[75] Inventors: Shiro Bito; Isami Hirao; Kazuhiko Oozeki; Minoru Tsuruta; Akito Mukaizawa; Akio Nakada; Tsuyoshi Tsukagoshi; Shuichi Kimura; Toshihiko Suzuta; Seiji Kuramoto, all of Tokyo, Japan

[73] Assignee: Olympus Optical Co., Ltd., Tokyo, Japan

[21] Appl. No.: 461,987

[22] Filed: Jun. 5, 1995

Related U.S. Application Data

[62] Division of Ser. No. 384,210, Feb. 3, 1995, abandoned, which is a continuation of Ser. No. 72,224, Jun. 3, 1993, abandoned.

[30] Foreign Application Priority Data

| Jun. 4, 1992 | [JP] | Japan | 4-144299 |
| Jun. 4, 1992 | [JP] | Japan | 4-144640 |
| Mar. 31, 1993 | [JP] | Japan | 5-094963 |

[51] Int. Cl.⁶ .................................................. A61B 17/10
[52] U.S. Cl. ....................... 606/139; 606/142; 606/144; 606/148; 606/151
[58] Field of Search ........................... 606/139, 140, 606/141, 142, 144, 148, 151, 154, 157

[56] References Cited

U.S. PATENT DOCUMENTS

| 3,513,848 | 5/1970 | Winston et al. |
| 4,487,205 | 12/1984 | Di Giovanni et al. |
| 4,498,476 | 2/1985 | Cerwin et al. |
| 4,805,618 | 2/1989 | Ueda et al. |
| 4,983,177 | 1/1991 | Wolf. |
| 5,005,749 | 4/1991 | Aranyi. |
| 5,040,715 | 8/1991 | Green et al. |
| 5,084,057 | 1/1992 | Green et al. |
| 5,100,420 | 3/1992 | Green et al. |
| 5,171,251 | 12/1992 | Bregen et al. |
| 5,171,252 | 12/1992 | Friedland. |
| 5,201,900 | 4/1993 | Nardella. |
| 5,207,691 | 5/1993 | Nardella. |
| 5,306,280 | 4/1994 | Bregen et al. ........................... 606/143 |
| 5,383,883 | 1/1995 | Wilk et al. ................................ 606/142 |

FOREIGN PATENT DOCUMENTS

| 57-112856 | 7/1982 | Japan. |
| 3-12126 | 1/1991 | Japan. |

OTHER PUBLICATIONS

Encyclopedia of Polymer Science and Engineering, vol. 1, John Wiley & Sons, Copyright 1985, Title and copyright pages and pp. 525-530.

Primary Examiner—Michael Buiz
Assistant Examiner—Mark S. Leonardo
Attorney, Agent, or Firm—Frishauf, Holtz, Goodman, Langer & Chick

[57] ABSTRACT

A surgical instrument for fastening together opposing portions of a body organ. The instrument comprises a first support for supporting the first opposing portion of the body organ, a second support opposing the first support, for supporting the second opposing portion of the body organ, and a displacement-preventing member connected to the first or second support for preventing the supports from displacing relative to each other. The member comprises a pin protruding from one of the supports and a hole formed in the other of the supports. The pin is made of thermoplastic resin. When heated, the pins is softened and deformed, whereby the first and second supports are secured to each other, fastening together the opposing portions of the body organ.

36 Claims, 29 Drawing Sheets

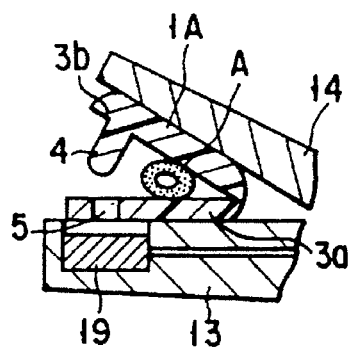
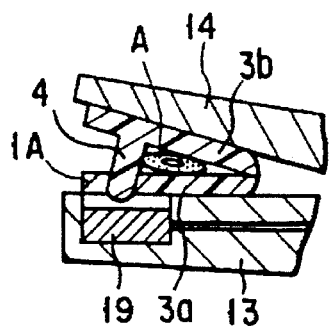
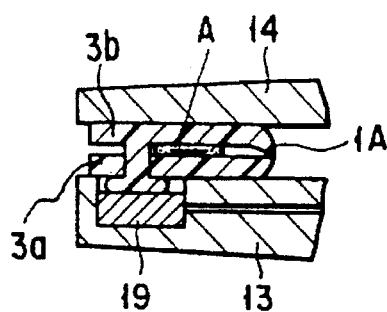
FIG. 5A     FIG. 5B     FIG. 5C
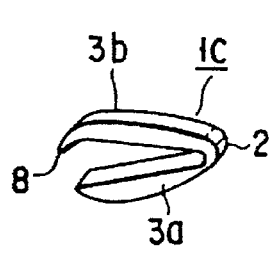
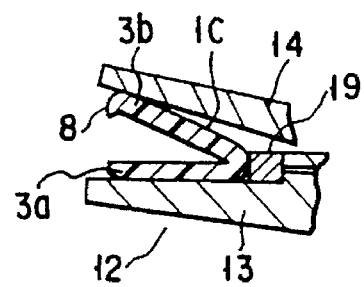
FIG. 6     FIG. 7
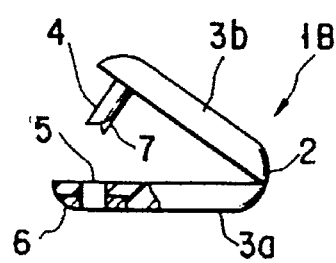
FIG. 8A
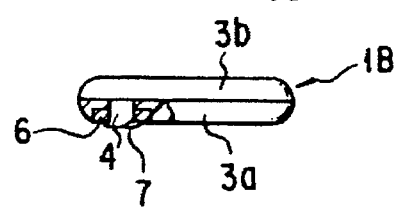
FIG. 8B

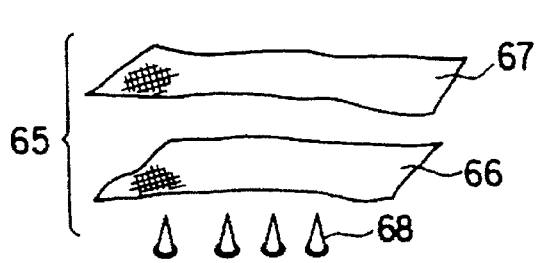
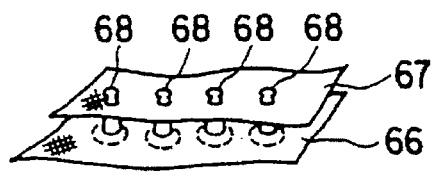
FIG. 18A    FIG. 18B
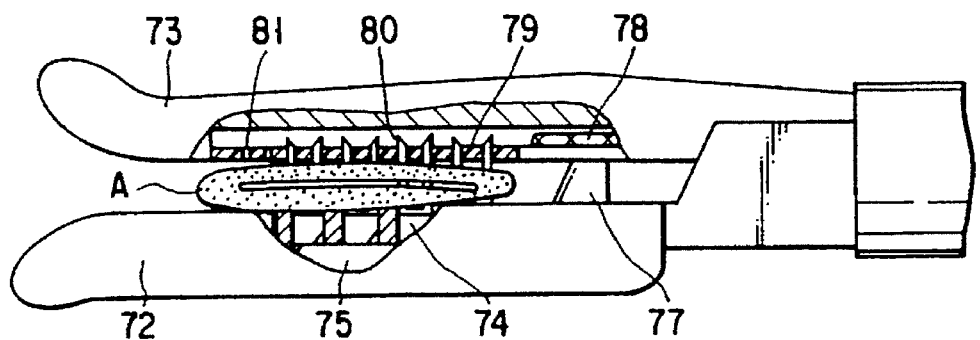
FIG. 19
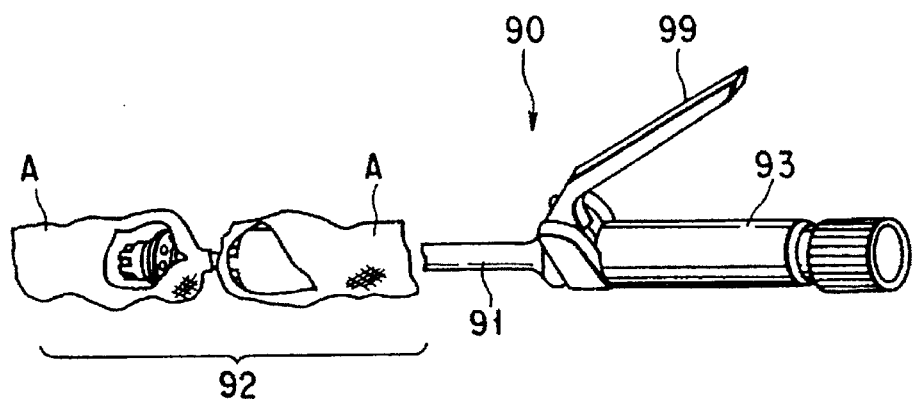
FIG. 20

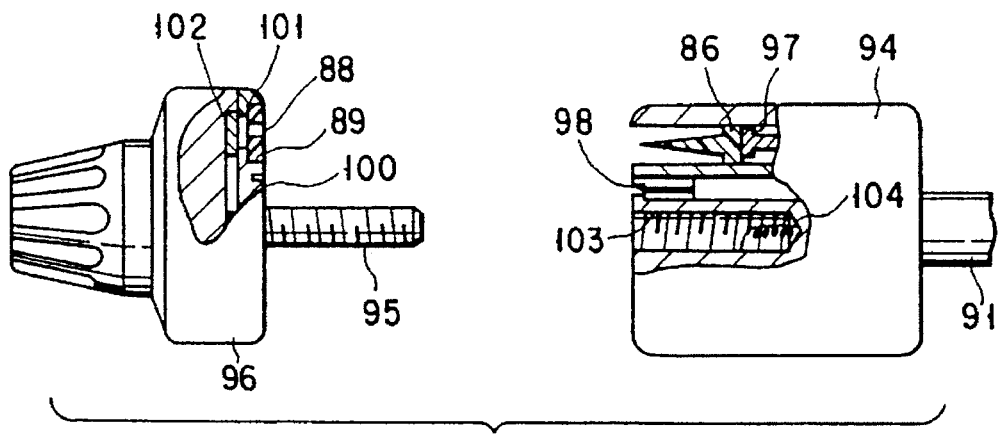
F I G. 21
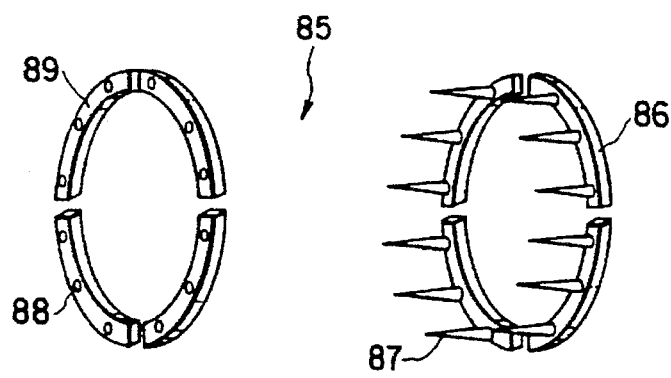
F I G. 22
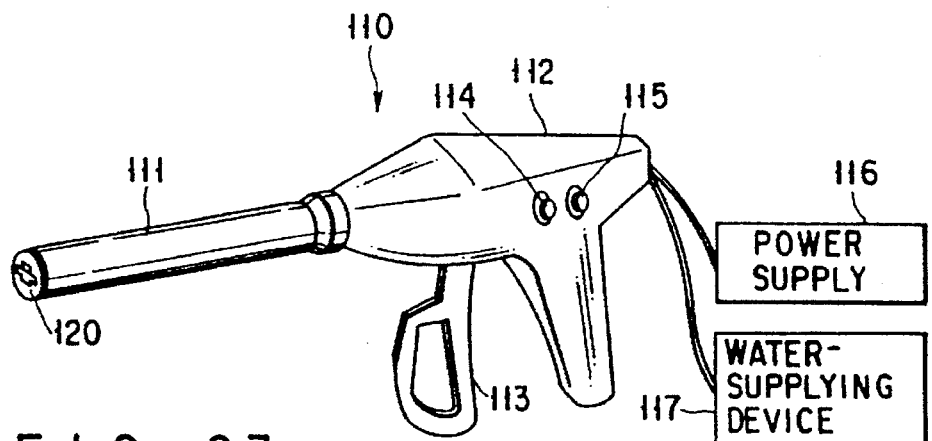
F I G. 23

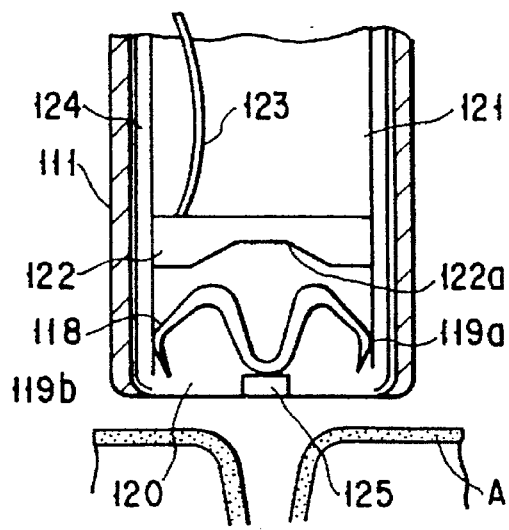
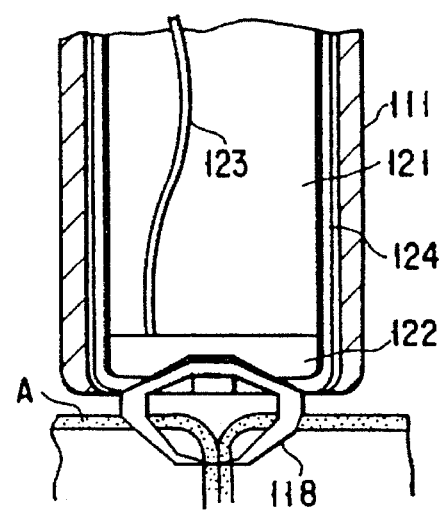
F I G. 24A          F I G. 24B
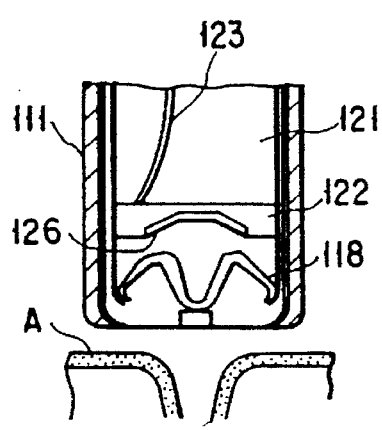
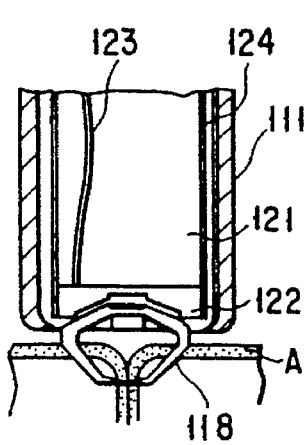
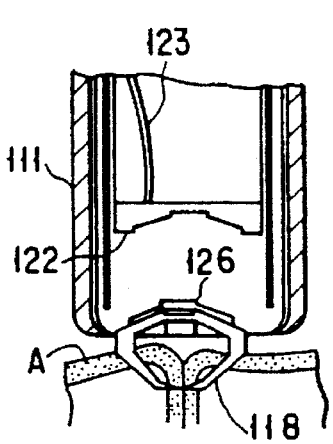
FIG. 25A          FIG. 25B          FIG. 25C
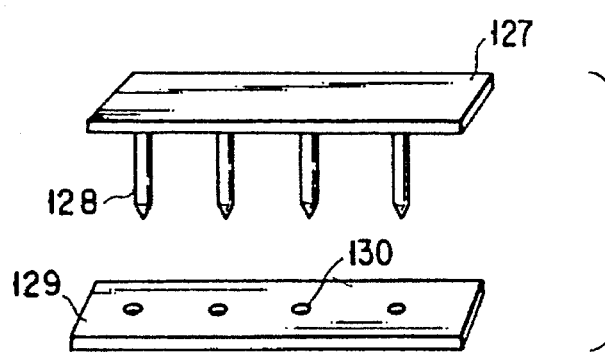
F I G. 26

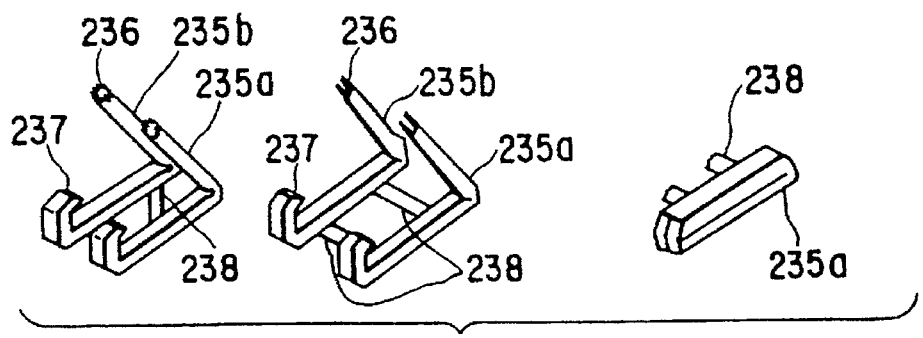
F I G. 52
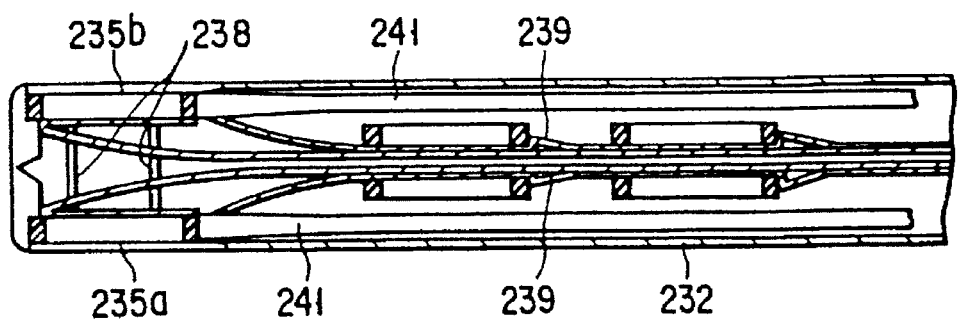
F I G. 53
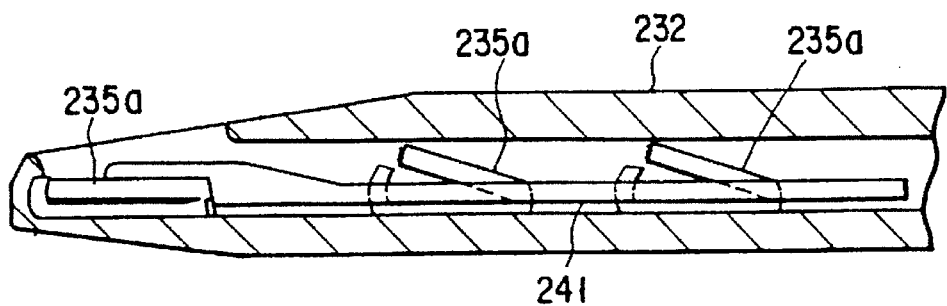
F I G. 54
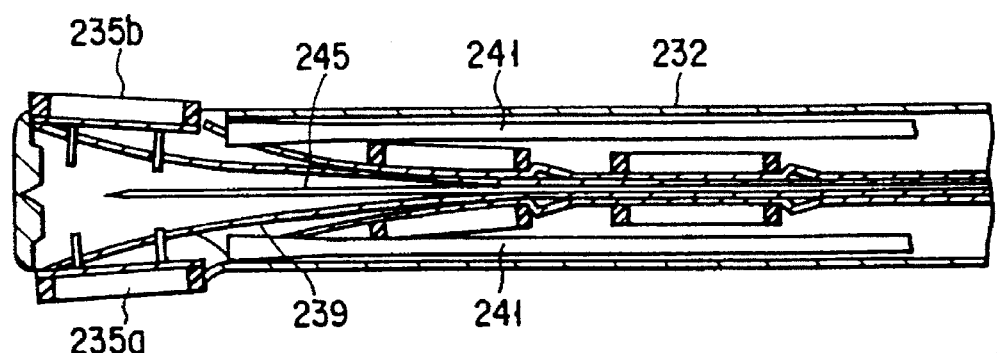
F I G. 55

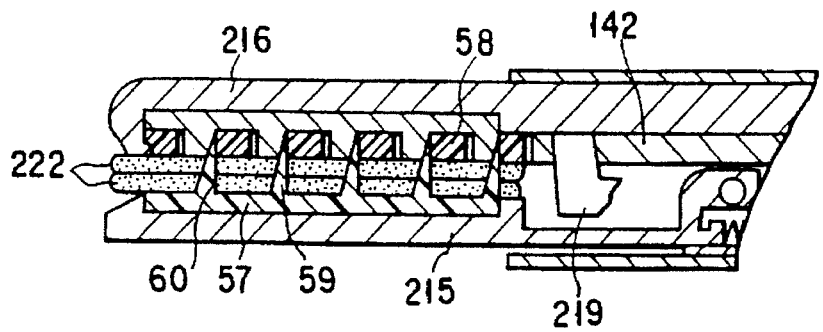
F I G. 58
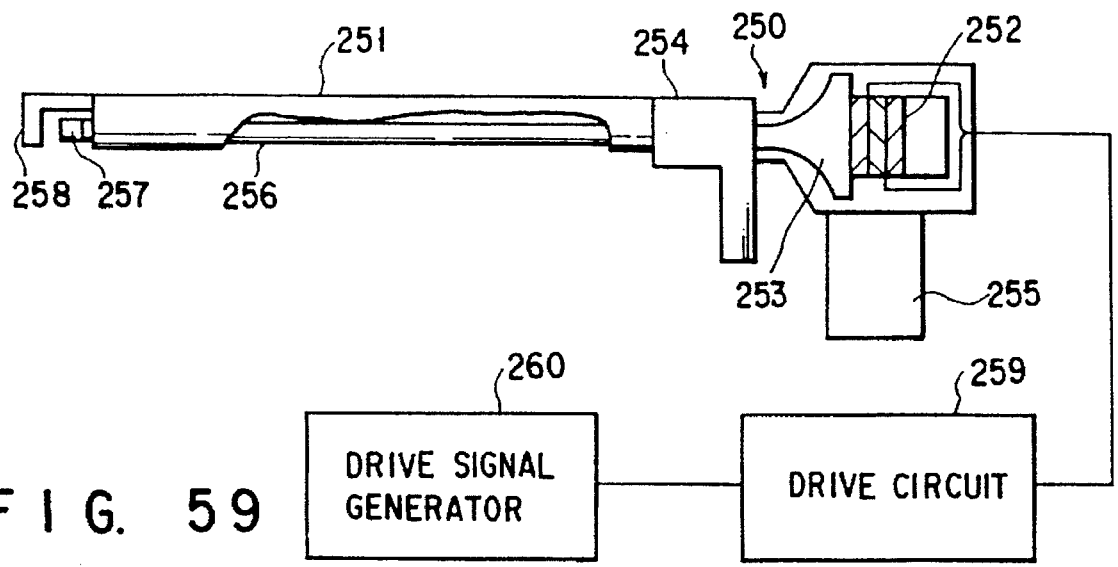
F I G. 59
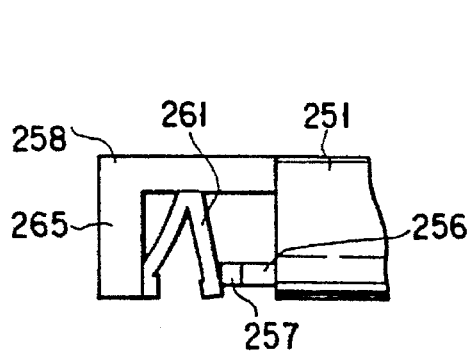
F I G. 60
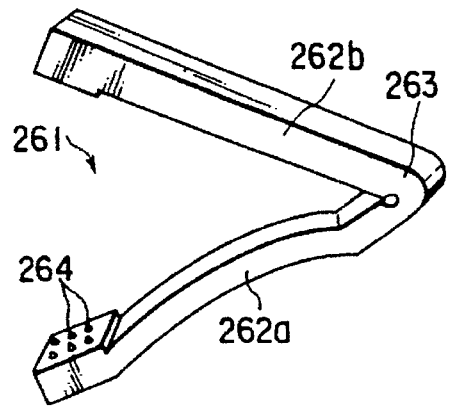
F I G. 61

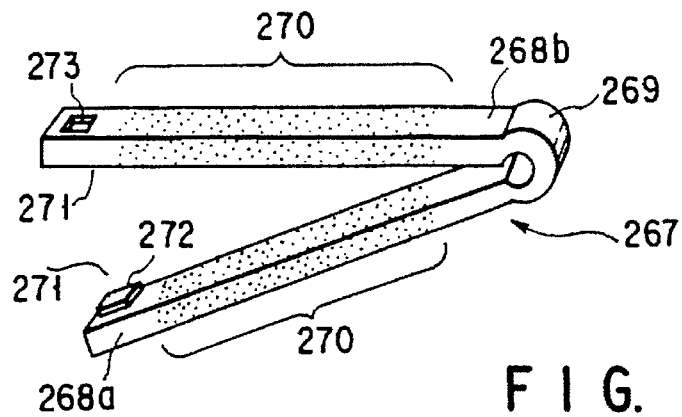
F I G. 62
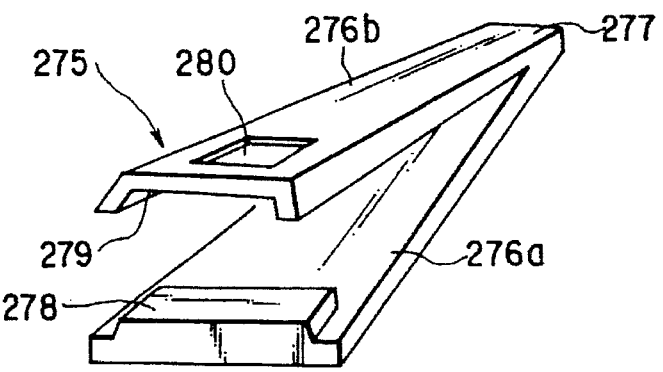
F I G. 63
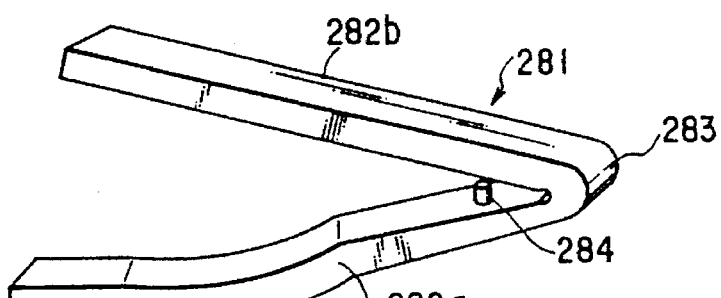
F I G. 64
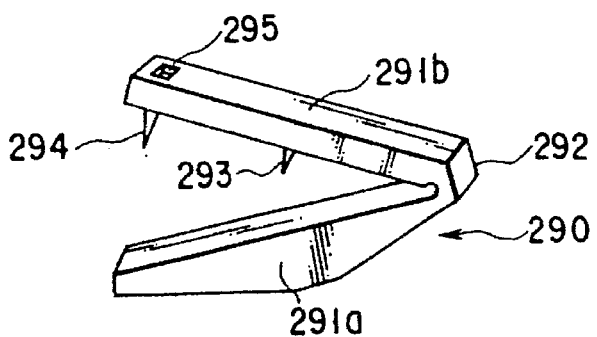
F I G. 65

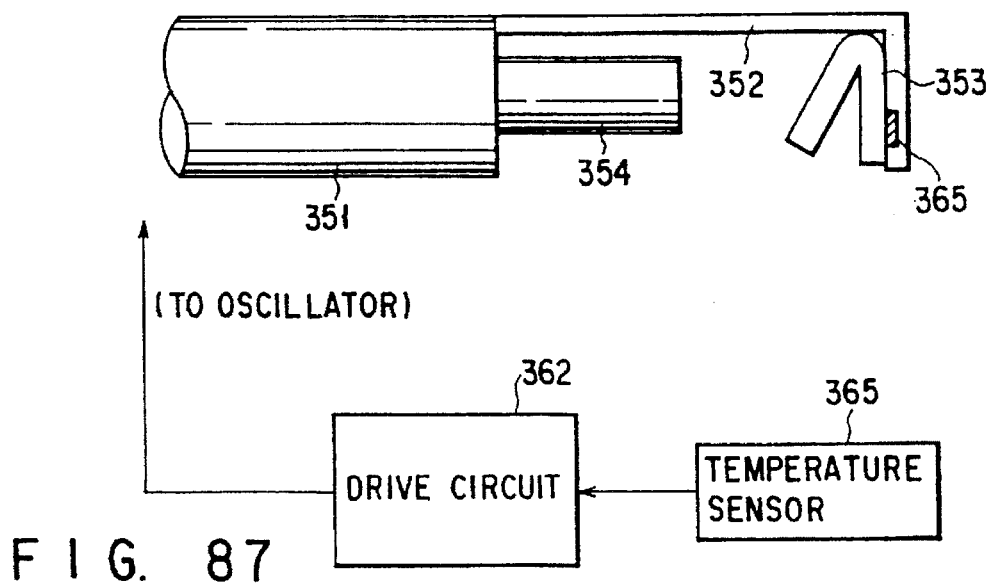
F I G. 87
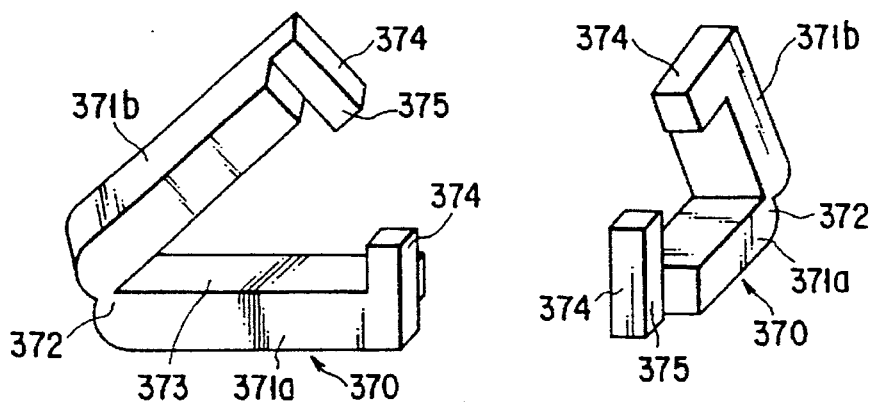
F I G. 88A
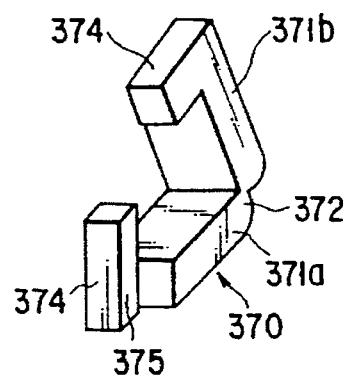
F I G. 88B
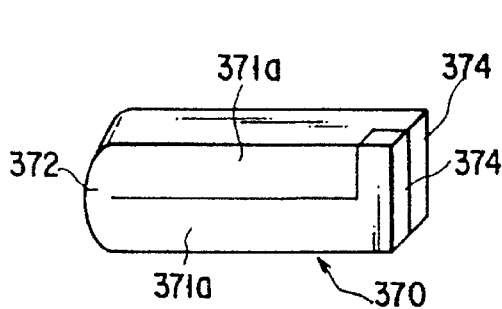
F I G. 89A
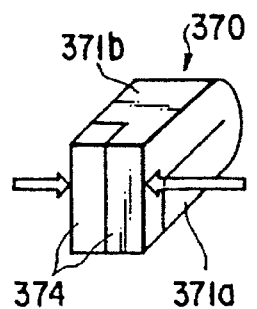
F I G. 89B

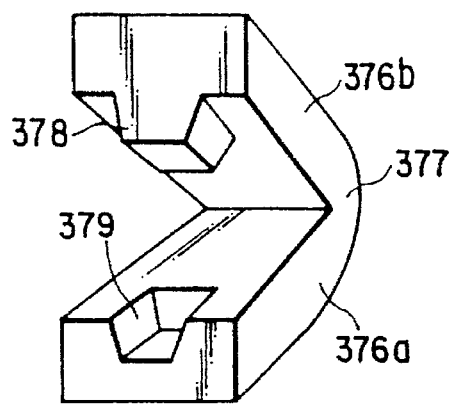
F I G. 90
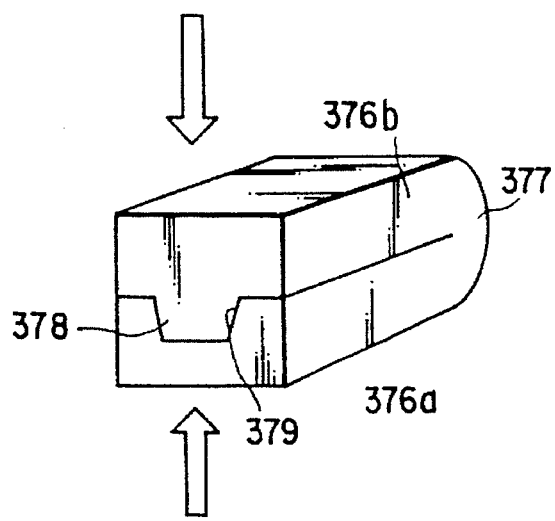
F I G. 91
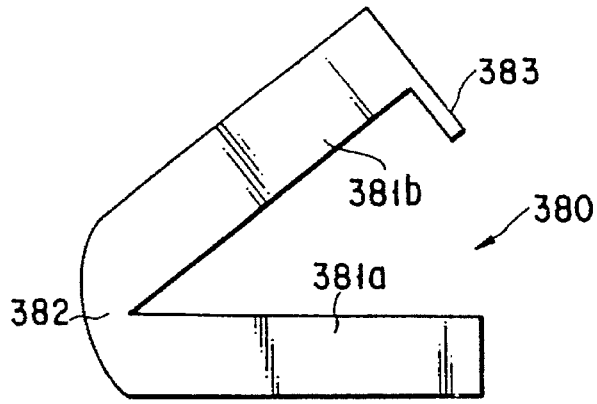
F I G. 92
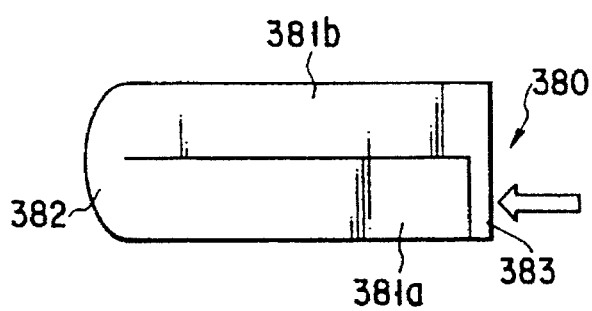
F I G. 93
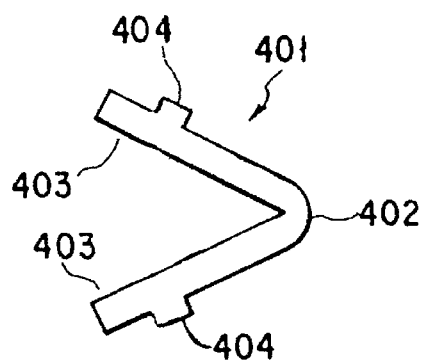
F I G. 94

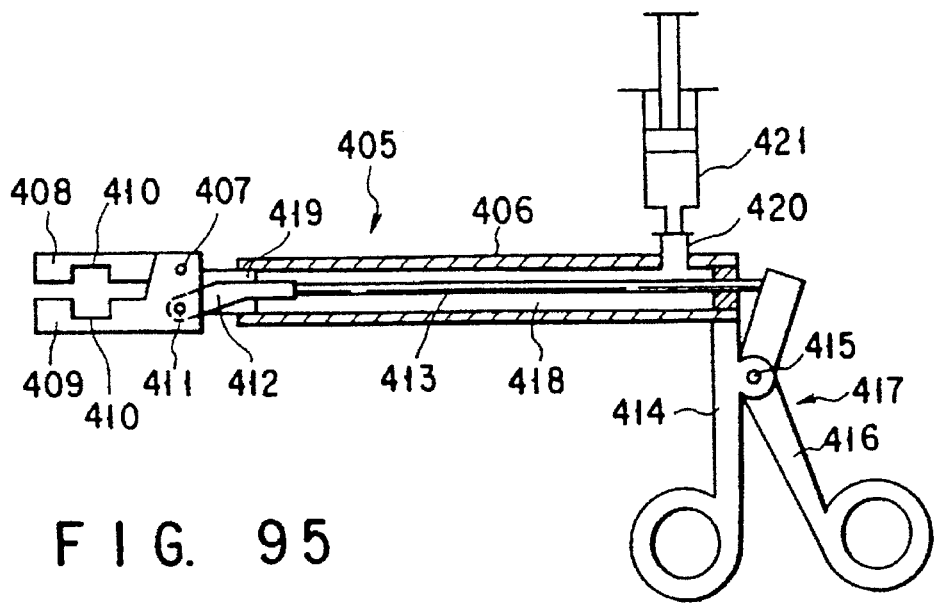
F I G. 95
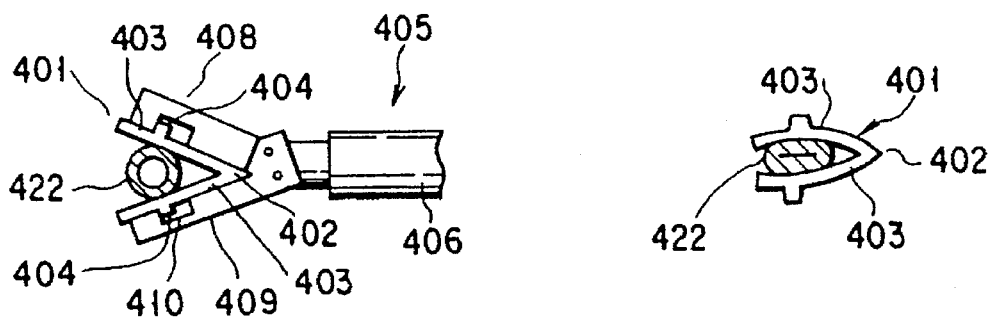
F I G. 96
F I G. 97
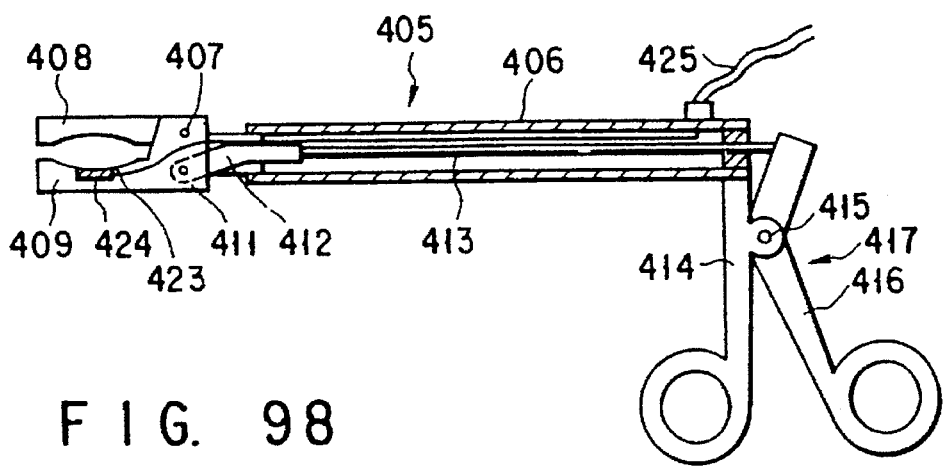
F I G. 98

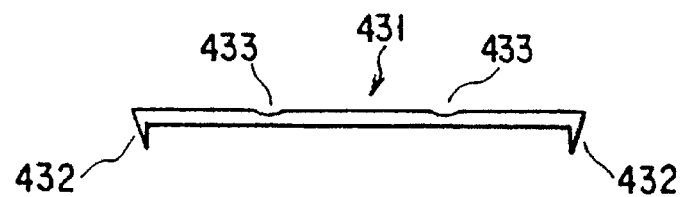
F I G. 99
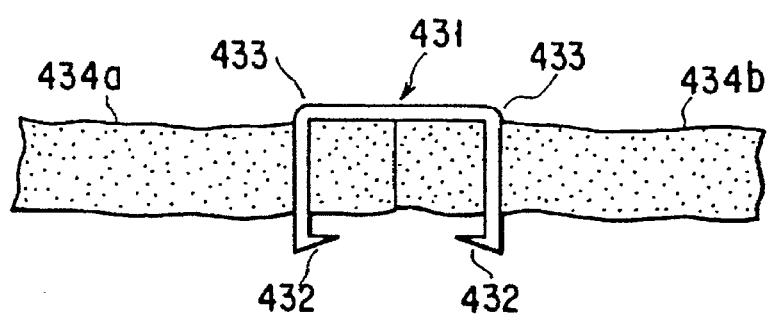
F I G. 100
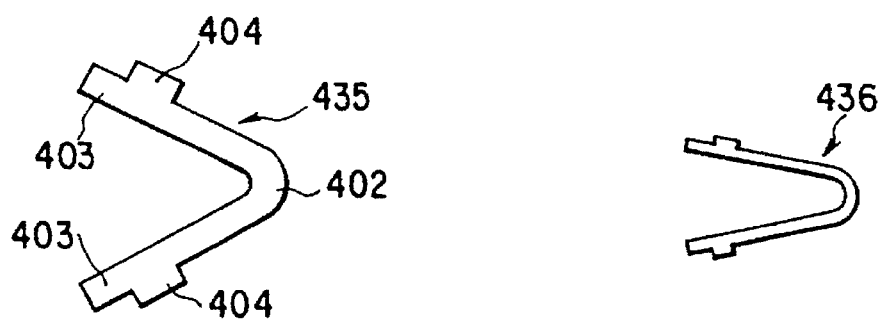
F I G. 101     F I G. 102

TISSUE-FIXING SURGICAL DEVICE, AND METHOD OF FIXING TISSUES

This is a division of application Ser. No. 08/384,210, filed Feb. 3, 1995, now abandoned which is a Continuation of Application Ser. No. 08/072,224, filed Jun. 3, 1993, now abandoned.

BACKGROUND OF THE INVENTION

1. Field of the Invention

The present invention relates to a surgical instrument for ligating or suturing tissues, a device for ligating or suturing tissues together, and a method of ligating or suturing tissues.

2. Description of the Related Art

Hitherto, clips applicators of the type shown in Published Unexamined Jpn. Pat. Appln. Publication No. 57-112856 have been used to ligate tubular organs such as blood vessels and bile ducts by using clips. Staplers of the type disclosed in Published Unexamined Jpn. Pat. Appln. Publication No. 3-12126 have been used to suture tubular organs such as intestines by using staples.

Most clips and staplers used for ligating and suturing tissues are made of metal, such as titanium, which is compatible with body tissues. Clips are known which are made of resin capable of being absorbed into body tissues, such as polydioxanone, polylactide, or polyglycolide.

Although the clips and staples are made of metal compatible with tissues, such as titanium, they will remain as foreign bodies in patients. Clips made of resin capable of being absorbed into body tissues are more likely to become loose than those made of metal, because their latching or clamping force is relatively small since it results from the elasticity of the resin.

SUMMARY OF THE INVENTION

The object of this invention is to provide a surgical instrument which can reliably ligate or suture tissues with devices such as clips or staples, a device which can ligate or suture tissues steadfastly, and a method which can reliably ligate or suture tissues.

To attained the object, there are provided the following apparatus, devices and methods according to the present invention:

A surgical instrument for fastening together opposing portions of a body organ, comprising: first support means for supporting the first opposing portion of the body organ; second support means opposing the first support means, for supporting the second opposing portion of the body organ; displacement-preventing means connected to one of the support means for preventing the support means from displacing relative to each other, and made of thermoplastic resin which is softened when heated; and an applicator having holding means for holding at least one of the support means, heating means for heating and softening the displacement-preventing means, and operating means for deforming the displacement-preventing means thus softened, thereby to fix the first and second support means in position to fasten together the opposing portions of the body organ.

A surgical device for fastening together opposing portions of a body organ, comprising: first support means for supporting the first opposing portion of the body organ; second support means opposing the first support means, for supporting the second opposing portion of the body organ; and displacement-preventing means connected to one of the support means for preventing the support means from displacing relative to each other, and made of thermoplastic resin which is softened when heated.

A method of applying a clip to a body organ by means of an applicator, comprising the steps of: preparing a clip comprising a pair of legs and a thermally deformable member, all made of thermoplastic resin; loading the clip in the applicator; placing the body organ between the legs of the clip; heating and softening the thermally deformable member; and closing the legs of the clip, thereby clamping the body organ.

A method of applying a fastener to body tissues by means of an applicator, for fastening the body tissues together, comprising the steps of: preparing a fastener made of thermoplastic resin and having legs; loading the fastener in the applicator; piercing the legs of the fastener through the body tissues; and heating and deforming the legs of the fastener, thereby fastening the body tissues together.

A method of applying a fastener and a retainer to body tissues by means of an applicator, for fastening the body tissues together, comprising the steps of: preparing the fastener and the retainer, both made of thermoplastic resin; loading the fastener and the retainer in the applicator; piercing the legs of the fastener through the body tissues; connecting the legs of the fastener to the retainer; and heating and deforming the legs of the fastener, thereby securing the same to the retainer, thereby fastening the body tissues together.

With the present invention it is possible to clamp a tissue with a device made of thermoplastic resin, such as a clip or a staple, thereby achieving reliable ligation or suture of the tissue.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 5A, 5B, and 5C are diagrams explaining how to operate the clip applicator of FIG. 1;

FIG. 6 is a perspective view showing a clip to be applied by a clip applicator according to a second embodiment of the invention;

FIG. 7 is a sectional view showing a part of the clip holder of the applicator which is the second embodiment of this invention;

FIGS. 8A and 8B are side views showing a modification of the clip shown in FIG. 6;

FIGS. 18A and 18B are perspective views, both showing the staple applied by the stapler of FIG. 16 and also explaining how to suture a organ tissue with this staple;

FIG. 19 is a partially sectional side view showing the distal end portion of a stapler which is a sixth embodiment of the present invention;

FIG. 20 is a perspective view showing a stapler which is a seventh embodiment of the invention;

FIG. 21 is an exploded view showing the suture section of the stapler shown in FIG. 20;

FIG. 22 is an exploded view of a stapler which is applied by the stapler shown in FIG. 20;

FIG. 23 is a perspective view of a stapler according to an eighth embodiment of this invention;

FIGS. 24A and 24B are cross-sectional views showing the distal end portion of the stapler shown in FIG. 23 and explaining how the stapler applies a staple to fasten body walls together;

FIGS. 25A, 25B, and 25C are cross-sectional views showing a modification of the stapler shown in FIG. 23;

FIG. 26 is an exploded view showing a first modification of the staple which is applied by the stapler shown in FIG. 12;

FIG. 52 is a perspective view showing clips to be applied by the applicator of FIG. 48;

FIG. 53 is a diagram explaining how to manipulate the clip applicator of FIG. 48;

FIG. 54 is another diagram explaining how to manipulate the clip applicator of FIG. 48;

FIG. 55 is still another diagram explaining how to manipulate the clip applicator of FIG. 48;

FIG. 58 is a sectional view of the distal end portion of the stapler shown in FIG. 56, explaining how the stapler applies staples;

FIG. 59 is a diagram schematically illustrating a clip applicator according to a seventeenth embodiment of this invention;

FIG. 60 is a side view showing the distal end portion of the clip applicator shown in FIG. 59;

FIG. 61 is a perspective view showing a clip to be applied by the applicator of FIG. 59;

FIG. 62 is a perspective view showing a clip which is an eighteenth embodiment of the present invention;

FIG. 63 is a perspective view illustrating a clip which is a nineteenth embodiment of the invention;

FIG. 64 is a perspective view showing a clip which is a twentieth embodiment of this invention;

FIG. 65 is a perspective view showing a clip which is to be applied by a clip applicator according to a twenty-first embodiment of the present invention;

FIG. 87 is a diagram schematically illustrating a clip applicator according to a thirty-third embodiment of this invention;

FIGS. 88A and 88B are perspective views, both showing a clip in open state, which is a thirty-fourth embodiment of this invention;

FIGS. 89A and 89B are perspective views, both showing the clip (FIGS. 88A and 88B) in closed state;

FIG. 90 is a perspective view showing a clip in open state, which is a thirty-fifth embodiment of the present invention;

FIG. 91 is a perspective view showing the clip (FIG. 90) in closed state;

FIG. 92 is a side view illustrating a clip in open state, which is a thirty-sixth embodiment of the present invention;

FIG. 93 is a side view showing the clip (FIG. 92) in closed position;

FIG. 94 is a side view showing a clip according to a thirty-seventh embodiment of the present invention;

FIG. 95 is a longitudinal sectional view showing a clip applicator which is the thirty-seventh embodiment of the invention and which is designed to apply the clip shown in FIG. 94;

FIG. 96 is a side view illustrating the clip-holding section of the applicator shown in FIG. 95;

FIG. 97 is a side view showing the clip (FIG. 94) which is clamping a tubular organ;

FIG. 98 is a longitudinal sectional view showing a clip applicator which is a thirty-eighth embodiment of the invention;

FIG. 99 is a side view showing a clip according to a thirty-ninth embodiment of the present invention which is applied by the clip applicator;

FIG. 100 is a view explaining how the clip of FIG. 99 stitches together two tissues;

FIG. 101 is a side view of a clip which is a fortieth embodiment of the present invention; and FIG. 102 is a side view of a clip which is a forty-first embodiment of the present invention.

DETAILED DESCRIPTION OF THE PREFERRED EMBODIMENTS

An clip applicator, which is a first embodiment of the present invention, will be described with reference to FIGS. 1 to 6. Of these figures, FIG. 2 shows a clip 1A which the applicator 10 will apply to ligate a tubular organ such as a blood vessel.

Figure 2:
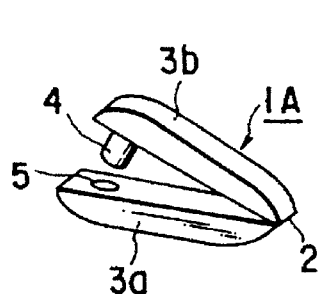
FIG. 2 is a perspective view showing a clip which is to applied by the application shown in FIG. 1.

As shown in FIG. 2, the clip 1A has a first leg 3a (first support means) and a second leg 3b (second support means). The legs 3a and 3b are hinged to each other at a hinge portion 2. The first leg 3a has a through hole 5. A pin 4 protrudes from the second leg 3b, extending toward the hole 5 of the first leg 3a. The legs 3a and 3b can be abut on each other, whereby the pin 4 is fixed, relatively tight in the hole 5 of the second leg 3a. The legs 3a and 3b are formed integral with each other, made of thermoplastic resin which is compatible with body tissues and which can be absorbed thereinto.

Figure 1:
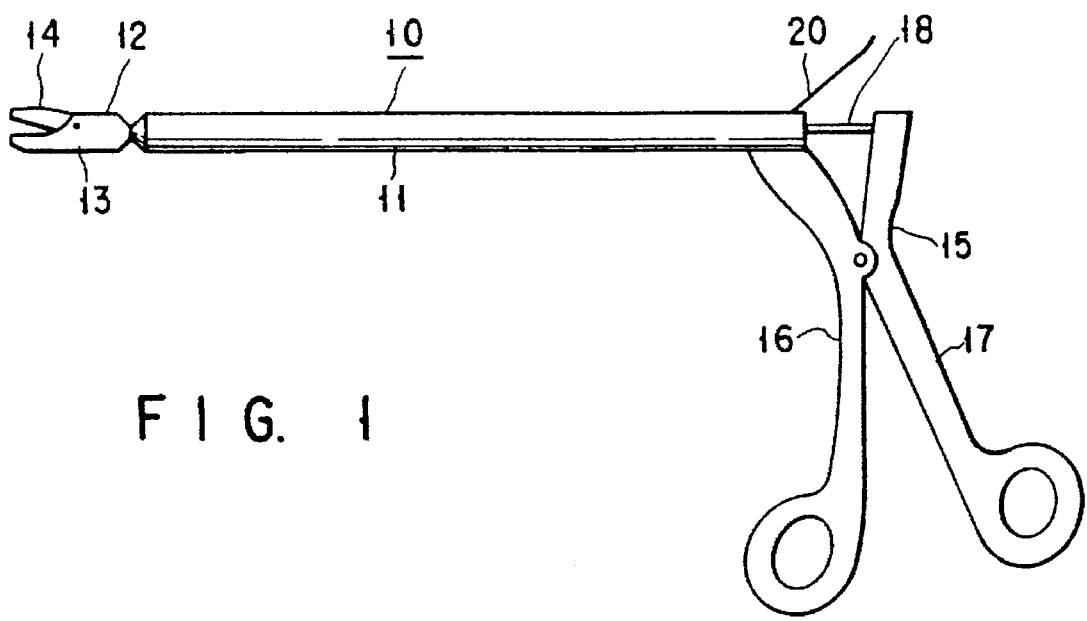
FIG. 1 is a side view showing a clip applicator which is a first embodiment of the present invention.
Figure 3:
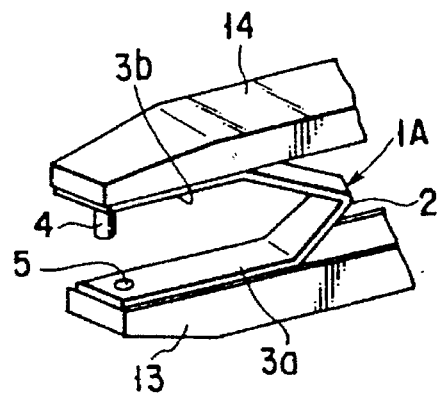
FIG. 3 is a perspective view showing the clip holder of the applicator shown in FIG. 1.

As shown in FIG. 1, the clip applicator 10 has a sheath 11 which will be inserted an abdominal cavity through a guide tube (not shown) such as a trocar. A clip holder 12 is attached to the distal end of the sheath 11, for holding the clip 1A. As FIG. 3 shows, the clip holder 12 comprises a first clip-holding member 13 secured to the sheath 11 and a second clip-holding member 14 connected by a pin to the first clip-holding member 13. The second clip-holding member 14 can rotate about the pin, whereby the clip holder 12 is opened and closed.

Referring back to FIG. 1, an operation section 15 is connected to the proximal end of the sheath 11. The section 15 is manipulated to open and close the clip holder 12 attached to the distal end of the sheath 11. The operation section 15 comprises a fixed handle 16 and a handle 17. The fixed handle 16 is fastened to the proximal end of the sheath 11. The handle 17 is coupled to the fixed handle 16 by a connecting pin, and can rotate around the connecting pin. A wire 18 made of comparatively hard material is connected at one end to the handle 17, extends through the sheath 11, and is connected at the other end to the proximal end of the second clip-holding member 14. Therefore, the handle 17 pulls the wire 18, closing the clip holder 12, when it is rotated in one direction, and pushes the wire 18, opening the clip holder 12, when it is rotated in the opposite direction.

Figure 4:
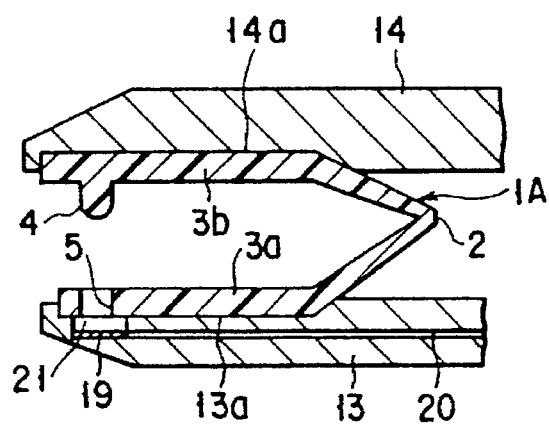
FIG. 4 is a sectional view showing a part of the clip holder of the applicator shown in FIG. 1.

As can be understood from FIGS. 3 and 4, the clip 1A is held between the clip-holding members 13 and 14 of the holder 12, so that it may be inserted into an abdominal cavity and applied therein. To be more specific, the legs 3a and 3b of the clip 1A are fitted, in part, in the recesses 13a and 14a formed in the opposing surfaces of the clip-holding members 13 and 14, respectively. Hence, the holder 12 holds clip 1A steadfastly.

As shown in FIG. 4, an electric heater 19 such as a diode or a ceramic heater 19 is embedded in that surface of the first clip-holding member 13 which opposes the second clip-holing member 14. The heater 19 is connected to one end of a power-supply cord 20, which is embedded in the first clip-holding member 13 and extends through the sheath 11 to the proximal end of the applicator 10. The cord 20 is connected, at its other end, to a power supply (not shown) located outside the applicator 10. The heater 19 is exposed through an escape hole 21 made in said surface of the first clip-holding member 13.

With reference to FIGS. 5A, 5B, and 5C, it will be described how the clip applicator 10 is operated to apply the clip 1A to ligate a tubular organ such as a blood vessel. The clip 1A is removed from a cartridge (not shown). As shown in FIG. 5A, the clip 1A is pinched in the gap between the clip-holding members 13 and 14 of the clip holder 12 which is attached to the distal end of the sheath 11.

Next, the sheath 11 is inserted into a body cavity where the tubular organ A is located. The clip applicator 10 is manipulated, thereby placing the tubular organ A in the gap between the legs 3a and 3b of the clip 1A as is illustrated in FIG. 5A. Then, the handle 17 is operated, rotating the second clip-holding member 14 of the clip holder 12 and thus closing the clip 1A. As a result, the pin 4 of the second leg 3b of the clip 1A fits into the through hole 5 of the first leg 3a, as is shown in FIG. 5B. The tubular organ A is thereby collapsed.

In this condition, an electric current is supplied from the power supply (not shown) to the heater 19 embedded in the first clip-holding member 13, by either automatic operation or manual operation. The heater 19 heats the tip of the pin 4 fitted in the hole 5. The tip of the pin 4 is thereby fused to the first leg 3a.

Once the pin 4 of the second leg 3b is fused to the first leg 3a, the clip 1A firmly clamps the tubular organ A. This prevents the clip 1A from becoming so loose as to release the tubular organ A.

Another clip applicator, which is a second embodiment of the invention, will be described with reference to FIGS. 6 and 7.

FIG. 6 shows a clip 1C used in this embodiment, and FIG. 7 shows the distal end portion of the clip holder 12 of the clip applicator. As can be understood from FIG. 6, the second leg 3b of the clip 1C has a claw 8 at its distal end. The claw 8 is so shaped as to latch the distal end of the first leg 3a of the clip 1C. As shown in FIG. 7, a heater 19 is located at the hinge portion of the clip 1C. After the clip 1C is closed, with the claw 8 latching the distal end of the first leg 3a, the heater 19 heats and softens the hinge portion. Then, the hinge portion is cooled, whereby the clip 1C is deformed permanently, with the legs 3a and 3b fastened together firmly.

FIGS. 8A and 8B show a modification 1B of the clip 1A shown in FIG. 2. The clip 1B differs from the clip 1A in two respects. First, that portion of the lower surface of the leg 3a which surround the hole 5 is made of heat-resistant resin 6. Second, the pin 4 has a flaring forked tip 7.

Even when the heat generated by the heater 19 is applied to the clip 1B, the leg 3a of the clip 1B is not fused. When the clip 1B is closed by operating the applicator 10, the two parts of the forked tip 7 are moved away from each other and, in this condition, and thermally deformed due to the heat generated by the heater 19. Once the forked tip 7 is so deformed, the pin 4 is prevented from slipping out of the hole 5, whereby legs 3a and 3b of the clip 1B are connected together firmly.

Figure 9:
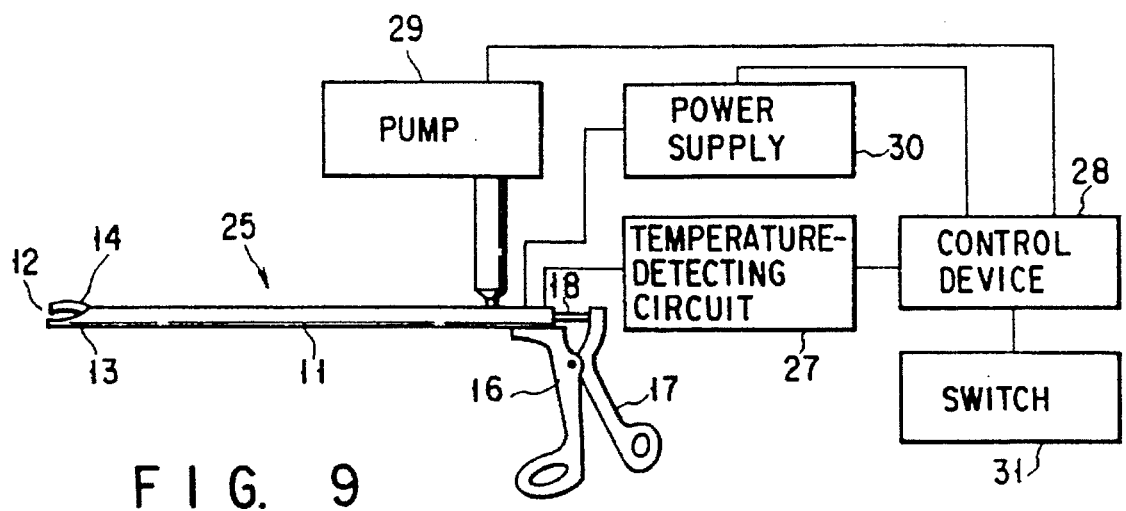
FIG. 9 is a diagram showing a clip applicator according to a third embodiment of this invention.

A clip applicator 25 according to a third embodiment of the invention will be described, with reference to FIGS. 9 and 10.

Figure 10:
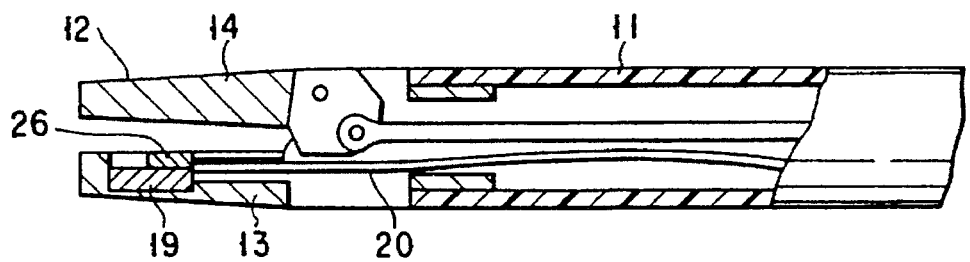
FIG. 10 is a sectional view showing the distal end portion of the clip applicator shown in FIG. 9.

As is evident from FIG. 10, a temperature sensor 26 is arranged near the heater 19 embedded in the first clip-holding member 13 of the clip holder 12. The sensor 26 is connected to a temperature-detecting circuit 27 shown in FIG. 9. The temperature data the circuit 27 has obtained is input to a control device 28. The device 28 controls a cooling-water pump 29 and a power supply 30 in accordance with the temperature data. The control device 28 is turned on or off by operating a switch 31. The pump 29 is connected to the proximal end portion of the sheath 11 of the applicator 25. The cooling water can thereby be supplied from the pump 29 to the clip holder 12 through the sheath 11. The clip applicator 25 is identical in any other structural features to the clip applicator 10 which is shown in FIG. 1.

The handle 17 is manipulated, thus closing the clip holder 12, hence, closing the clip 1A (not shown) held between the clip-holding members 13 and 14. As a result, the clip 1A clamps a tubular organ (not shown). Then, the switch 31 is closed, and the control device 28 supplies a signal to the power supply 30. In response to the signal the power supply 30 supplies a current the heater 19. The heater 19 generates heat. The heat is applied to the pin 4 which is inserted in the hole 5 of the leg 3a.

The temperature sensor 26 detects the temperature of the heater 19 and generates a signal representing this temperature. The signal is supplied to the temperature-detecting circuit 27, which produces temperature data from the signal. The data is input to the control device 28. When the temperature represented by the data exceeds a preset value, the circuit 28 outputs a temperature control signal, which turns off the power supply 30. The heater 19 can therefore be maintained at a temperature which is higher than the glass-transition point of the pin 4 and which is appropriate for thermally deforming the pin 4.

Upon lapse of a prescribed time after the temperature of the heater 19 has reached the predetermined value, said prescribed time being long enough for the pin 4 to fuse with first leg 3a, it is detected that the clip 1A has been thermally deformed. At this time, the control device 28 generates a power-supply stop signal and a pump drive signal. The power-supply stop signal and the pump drive signal are supplied to the power supply 30 and the cooling-water pump 29, respectively. In response to the stop signal, the power supply 30 stops supplying power to the heater 19. In response to the drive signal, the cooling-water pump 29 operates, supplying cooling water (e.g., physiological salt solution) to the clip holder 12 through the sheath 11. The water, thus supplied, cools the holder 12 holding the clip 1A.

Since the cooling water is supplied to the clip holder 12 and cools the clip 1A immediately after the pin 4 of the clip 1A is fused to the first leg 3a of the clip 1A, the thermally deformed portion of the clip 1A can be rendered rigid quickly. The clip 1A can therefore ligate the body tissue readily, within a short period of time.

A stapler 40, which is a fourth embodiment of the present invention and designed to suture body tissues, will be described with reference to FIGS. 11 to 15.

Figure 11:
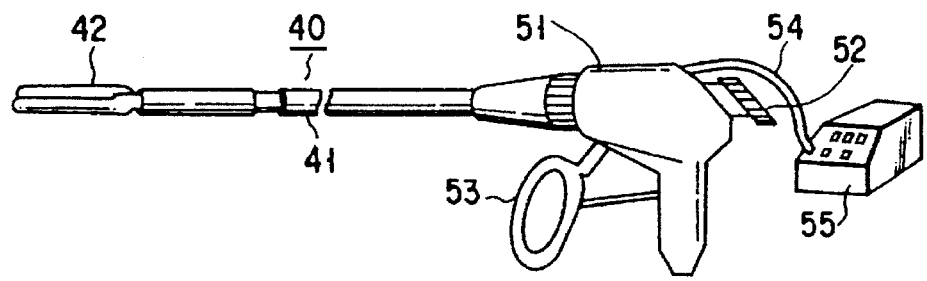
FIG. 11 is a side view showing a stapler which is a fourth embodiment of the present invention.

As FIG. 11 shows, the stapler 40 has an insertion section 41, a clamp section 42, and an operation section 51. The insertion section 41 is a sheath which is to be inserted into an abdominal cavity through a guiding instrument such as a trocar (not shown). The clamp section 42 designed for clamping body tissues is secured to the distal end of the insertion section 41.

Figure 12:
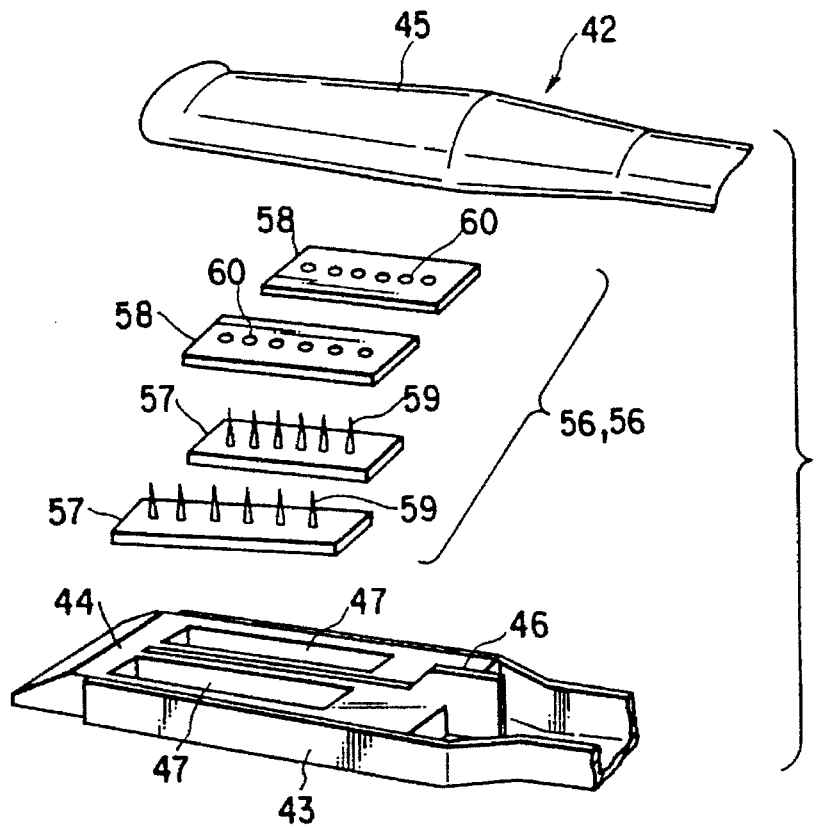
FIG. 12 is an exploded view showing the clamp section of the stapler illustrated in FIG. 11.
Figure 14:
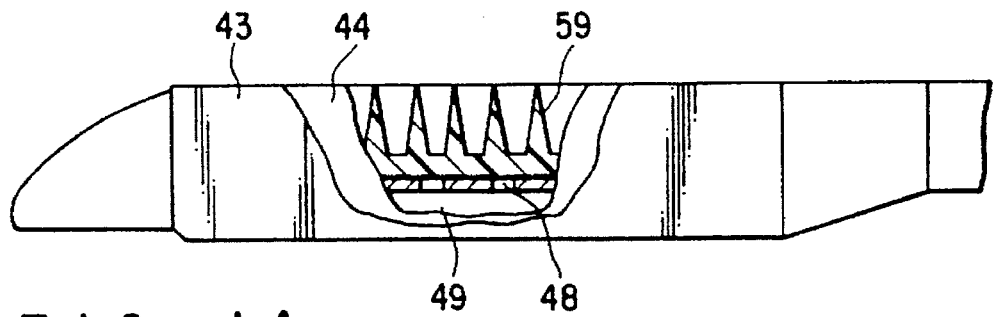
FIG. 14 is a partially sectional side view showing the cartridge of the clamp section.

As shown in FIG. 12, the section 42 comprises a casing 43, a cartridge 44, and an anvil 45. The casing 43 is secured to the distal end of the insertion section 41 and has an opening top. The cartridge 44 is removably contained in the casing 43. The anvil 45 opposes the upper surface of the cartridge 44 and can rotate to open and close the casing 43. The cartridge 44 has a knife-guiding groove 46 made in the upper surface, extending along the longitudinal axis of the casing 43. Two rectangular recesses 47 are made in the upper surface of the cartridge 44, located symmetrically with respect to the knife-guiding groove 46, for receiving staple bases 57 of a stapler 56 which will be described later. A knife (not shown) is moved forward, along the the knife-guiding groove 46. As is shown in FIG. 14, a plurality of gas nozzles 48 is formed in the bottom of each recess 47, for applying gas onto the staple base 57, thereby to push the base 57 upwards. As shown in FIG. 14, the cartridge 44 has a pusher-gas passage 49 through which to supply the gas for pushing the bases 57 upwards.

Figure 13:
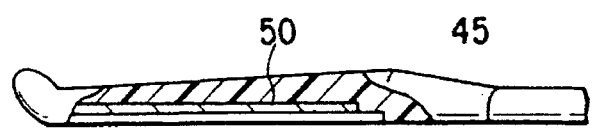
FIG. 13 is a partially sectional view showing the anvil of the clamp section shown in FIG. 12.

As shown in FIG. 13, a heater 50 is embedded in the lower surface of the anvil 45, which function as a stapler-holding surface. The heater 50 is used to thermally deform the tips of the staple pins 59 which stand upright on the staple bases 57 set in the recesses 47.

Referring back to FIG. 11, the operation section 51 is connected to the proximal end of the insertion section 41. The operation section 51 comprises an anvil-rotating handle 52 and a firing handle 53. The handle 52 is manipulated to rotate the anvil 45, thereby to open and close the clamp section 42. The firing handle 53 is squeezed to let the pusher gas flow from a gas cylinder (not shown) incorporated in the section 51 into the pusher-gas passage 49 of the cartridge 44. A power-supply cord 54, which is connected at one end to the heater 50, extends from the operating section 51 and is connected to a power supply 55.

As FIG. 12 shows, each staple 56 comprises a staple base (first support means) 57 and a plate-shaped staple cover (second support means) 58. A plurality of staple pins 59 stand upright on the staple base 57. The staple cover 58 has a plurality of holes 60 for receiving the staple pins 59. All components of each stable 56 are made of resin which is absorbable into body tissues.

It will be described how to apply the staples 56 by the stapler to stitch body tissues together. First, the cartridge 44 containing the bases of the staples 56 is placed in the casing 43 of the clamp section 42, and the staple covers. 58 are fitted in the anvil 45. Then, the clamp section 42 containing the staples 56 is attached to the distal end of the insertion section 41 of the stapler 40. The insertion section 41 is guided into a body cavity, thus locating the clamp section 42 at a desired position within the body cavity. The anvil-rotating handle 52 is manipulated, thereby opening the anvil 45. The clamp section 42 is moved until the body tissues B are clamped placed between the cartridge 44 and the anvil 45.

In this condition, the firing handle 53 is squeezed, making the pusher gas flow from the gas cylinder (not shown) into the recesses 47 made in the upper surface of the cartridge 44 through the pusher-gas passage 49 cut in the the cartridge 44. The gas pushes up the staple bases 57 placed in the recesses 47. As the staple bases 57 are thus pushed upwards, the staple pins 59 standing upright on the bases 57 pierce the tissues B and fit into the holes 60 of the staple covers 58.

Figure 15A:
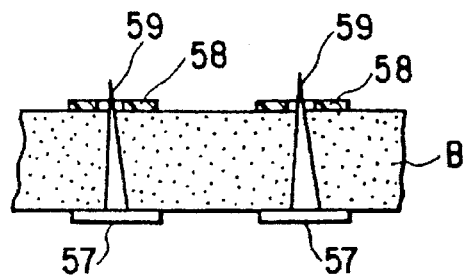
FIGS. 15A and 15B are diagrams explaining the operation of the stapler shown in FIG. 11.
Figure 15B:
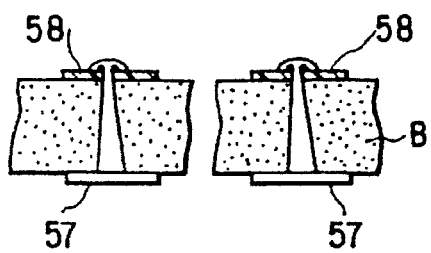

Then, a current is supplied from the power supply 55 to the heater 50. The heater 50 heats the tips of the staple pins 59 protruding from the holes 60 of the staple covers 58. The tips of the pins 59 fuse with the upper surface of the staple cover 58 as is shown in FIG. 15B which illustrates the body tissues B already cut with the knife (not shown) incorporated in the stapler 40.

As described above, the heater 50 embedded in the anvil 45 can fuse the tips of the staple pins 59, fastening the pins 59 to the upper surface of the staple covers 58. The staple bases 57 can thereby coupled to the staple covers 58 steadfastly. As a result, the body tissues B can be reliably fixed or clamped between each staple base 57 and the staple cover 58 associated therewith. Since the staple bases 57 and the staple covers 58 are made of resin which can be absorbed into tissues, they will be absorbed into the tissues B after the suture of the body tissues B.

Another stapler 70, which is a fifth embodiment of this invention, will be described with reference to FIGS. 16, 17, and 18.

The stapler 70 is designed to apply a staple 65 of the type shown in FIG. 18. The staple 65 comprises two net-like strips (support means) 66 and 67 and a plurality of staple pins (fastening means) 68. The strips 66 and 67 are made of heat-resistant material which can be absorbed into body tissues. The staple pins 68 are made of resin which is absorbable into body tissues. Each pin 68 has a proximal end 68a having a larger diameter than the remaining portion.

Figure 16:
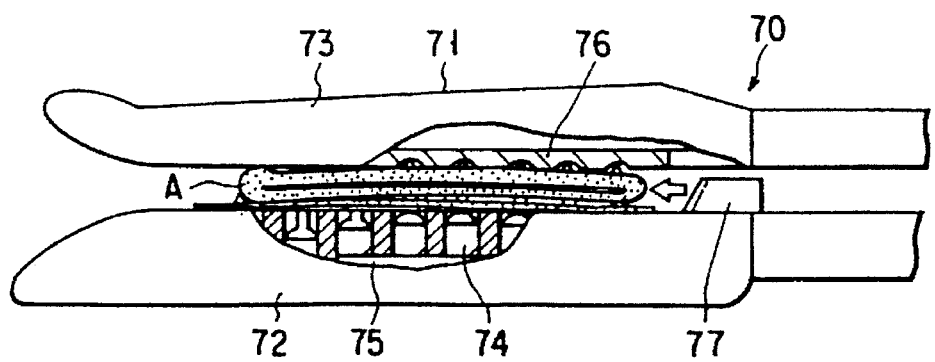
FIG. 16 is a partially sectional side view showing the distal end portion of a stapler which is a fifth embodiment of the present invention.

FIG. 16 is a partially sectional side view of the distal end portion of the stapler 70. As this figure shows, a clamp section 71 is connected to the distal end of the sheath of the stapler 70. The clamp section 71 is designed to clamp a tubular organ A such as a blood vessel. The section 71 comprises a cartridge 72 and an anvil 73. The cartridge 72, which is removable, contains the staple pins 68 and has pushers 74 and a pusher handle 75 for pushing the pushers 74 upwards, one after another. The anvil 73 is connected to the sheath and opposes the staple-holding surface (i.e., the upper surface) of the cartridge 72.

A heater 76 is arranged in the staple-holding surface (i.e., the lower surface) of the anvil 73, for heating and fusing the tips of the staple pins 68. As shown in FIG. 17, the net-like strips 66 and 67 are mounted on the staple-holding surface of the cartridge 72 and that of the anvil 73, respectively. The staple pins 68 are arranged in rows extending parallel to the axis of the cartridge 72. The pusher bar 75 extend also parallel to the axis of the cartridge 72 and can be moved back and forth. A knife 77 is mounted on the staple-holding surface of the cartridge 72. The knife 77 can be moved back and forth along the axis of the cartridge 72. When moved forward, it can cut a tubular organ A clamped between the cartridge 72 and the anvil 73.

To suture the tubular organ A with the staple 65 by means of the stapler 70, thus structured, the distal end portion of the stapler 70 is guided into a body cavity containing the tubular organ A. The clamp section 71 is then manipulated, thereby clamping the organ A between the cartridge 72 and the anvil 73. Next, the pusher bar 75 is slit forward by remote control, pushing the pushers 74 upwards one after another. The staple pins 73 are thereby pushed up, piercing the net-like strips 66, the organ A, and the net-like strip 67 and abutting the staple-holding surface of the anvil 73, as is shown in FIG. 17. In this condition, the heater 76 is turned on, heating and fusing the tips of the staple pins 68. As a result, the tips of the pins 68 collapse between the anvil 73 and the net-like strip 67 as shown in FIG. 18B. At the same time the tips of the pins 68 are so fused, the knife 77 is moved forward, thus cutting the tubular organ A along the row of of staple pins 68.

In this way, the stapler 70 can suture the tubular organ A with the staple 65, as steadfastly as does the stapler 40 shown in FIGS. 11 to 14.

Still another stapler, which is a sixth embodiment of the present invention, will be described with reference to FIG. 19.

Figure 17:
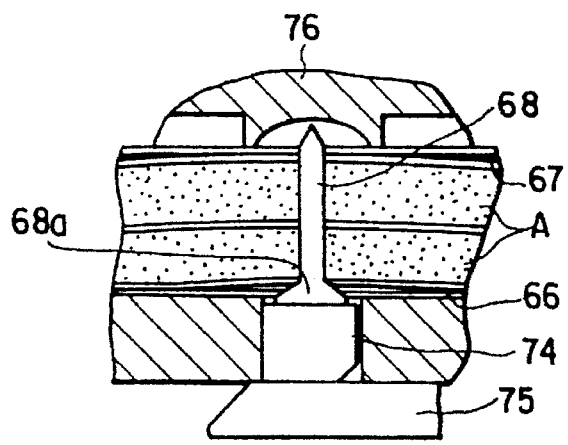
FIG. 17 is a cross-sectional view showing part of the clamp section of the stapler shown in FIG. 16, and explaining how to suture a tubular organ by means of the stapler.

Referring to FIG. 19, the clamp section of this stapler comprises a cartridge 72, an anvil 73, a pusher 74, a pusher bar 75, and a knife 77, which are identical to those of the stapler shown in FIG. 17. The clamp section has a heater 78 which can slide back and forth in the passage formed within the anvil 73, along the axis of the anvil 73. The heater 78 is used to heat the tips of U-shaped staples 80 made of resin which is absorbable into body tissues. A staple-receiving plate 79 is mounted on the lower surface of the anvil 73. The plate 79 is made of heat-resistant material and has a plurality of through holes 81 for receiving the tips of the staples 80.

This stapler is manipulated in the same way as the stapler. The sliding heater 78 located in the anvil 73 can locally heat the tips of each staple 80 partly inserted in the through holes 81 of the staple-receiving plate 79. As a result, the tips of the staples 80 are fused onto the upper surface of the plate 79, whereby the stapler can suture the tubular organ A with the staple 80, as steadfastly as does the stapler 70 (FIG. 16) which is the fifth embodiment of the invention.

A circular stapler 90, which is a seventh embodiment of this invention, will be described with reference to FIGS. 20, 21, and 22.

FIG. 22 is an exploded view showing a staple 85 which this stapler 90 apply to stitch tubular organs together. The staple 85 comprises a ring-shaped base 86, a plurality of pins 87, and a ring-shaped cover 89. The base 86 consists of four arcuate segments. The pins 87 protrude from the base 86 in parallel to one another and spaced apart in the circumferential direction of the base 86. The cover 89 also consists of four arcuate segments, each having the same number of pin-receiving holes 88. All components of the staple 85 are made of thermoplastic resin which can be absorbed into body tissues or which is compatible with body tissues.

As is shown in FIG. 20, the circular stapler 90 comprises an insertion section 91 which is to be inserted into a tubular organ A, a suture section 92 connected to the distal end of the insertion section 91, and an operation section 93 connected to the proximal end of the insertion section 91. The suture section 92 comprises a staple-feeding section 94 and a staple-receiving section 96, as is illustrated in FIG. 21. The staple-feeding section 94 is fastened to the insertion section 91. The staple-receiving section 96 is coupled to the distal end of the section 94 by a connecting bolt 95.

The staple-feeding section 94 contains a staple pusher 97 for pushing the staple base 86 forward, and a cylindrical cutter 98 for cutting off any unnecessary portions of the tubular organ A after the two severed parts of the organ A are stitched together. Both the staple pusher 97 and the circular cutter 98 can be driven back and forth by means of a hydraulic cylinder (not shown). As shown in FIG. 20, a handle 99 is connected to the operation section 93, for operating the hydraulic cylinder.

Referring to FIG. 21, the staple-receiving section 96 has a staple-holding surface 100 for holding the pins 87 which protrude from the base 86 pushed forward from the staple-feeding section 94. Formed in the surface 100 is a staple-holding groove 101 designed for holding the ring-shaped cover 89 of the staple 85. A heater 102 is placed at the bottom of the groove 101, for heating the tips of the staple pins 87.

The staple-feeding section 94 has a screw hole 103 which is cut in its the distal end and which is coaxial with the section 94. The connecting bolt 95 is set in screw engagement with the hole 103, coupling the staple-receiving section 96 to the distal end of the section 94. Arranged within the screw hole 103 is an electrically conductive spring 104, which extends through the connecting bolt 95 and is connected to the heater 102, for supplying electric power to the heater 102.

The stapler 90, thus constructed, is operated as follows, in order to stitch together two severed parts of the tubular organ A. As shown in FIG. 20, the insertion section 92 is inserted into the tubular organ A until the staple-feeding section 94 and the staple-receiving section 96 are placed within said two severed parts, respectively. In this condition, the severed edges of the organ parts, which have shrunk and collapsed, are located between the sections 94 and 96.

The handle 99 is squeezed, driving the staple pusher 97 forward. The staple base 86 is thereby pushed forward, whereby the staple pins 87 pierce the severed edges of the organ parts, are then inserted into the pin-receiving holes 88 of the ring-shaped cover 89, and finally abut on the heater 102 arranged in the staple-receiving section 96. In this condition, an electric current is supplied to the heater 102, which heats the tips of the pins 87. The tips of the pins 87 are thereby fused onto the ring-shaped cover 89. As a result, the severed parts of the tubular organ A are fastened together. Thereafter, the cylindrical cutter 98 is thrust forward, cutting the unnecessary portions from the sutured parts.

The circular stapler 90 can, therefore, achieve the same advantages as the stapler (FIG. 19) which is the sixth embodiment of the present invention.

Another stapler 110, which is an eighth embodiment of the invention, will be described with reference to FIGS. 23 and FIGS. 24A and 24B. As FIG. 23 shows, this stapler 110 comprises an insertion section 111 and an operation section 112. The operation section 112 is connected to the proximal end of the insertion section 111, and has a handle 113, a heater switch 114, and a water-supply switch 115. A power supply 116 and a water-supplying device 117 are connected to the operation section 112.

FIGS. 24A and 24B are cross-sectional views showing the internal structure of the distal end portion of the insertion section 111. The distal end portion of the section 111 contains a generally M-shaped staple 118. The staple 118 is made of thermoplastic resin which is absorbable into, or is compatible with, body tissues. The staple 118 has claws 119a and 119a, each at one end, which are sharp enough to piece body walls A and which can fasten body walls together.

The distal end portion of the insertion section 111 contains a staple pusher 121 which can be driven back and forth along the axis of the insertion section 111, for pushing the staple 118 from the insertion section 111 through a staple-feeding hole 120 made in the distal end of the insertion section 111. A heater 122 is attached to the distal end of the staple pusher 121. The heater 122 is connected to the power supply 116 by a cable 123 and has, in its front, a recess 122a. The recess 112a has the same shape as the staple 118, for holding the staple 118.

The insertion section 111 contains a tube 124, through which the water-supplying device 117 supplies cooling water to the distal end of the insertion section 111, thereby to cool the staple 118. An anvil 125 is located in the distal end of the section 111. The anvil 125 has a flange for supporting the center portion of the staple 118. The flange functions to hold the center portion of the staple 118.

The stapler 110, thus constructed, is operated as follows, in order to fasten the body walls A together. First, the insertion section 111 is so positioned that the the staple-feeding hole 120 is directed to the body walls A to be stitched together. Then, the handle 113 of the operation section 112 is squeezed, driving the staple pusher 121 to the distal end of the section 111. The pusher 121 subsequently pushes the center portion of the staple 118 against the anvil 125 as is shown in FIG. 24A. Pushed further, the staple 118 is bent or closed, whereby its claws 119a and 119b pierce the body walls A and finally abut on each other, piercing the walls A at other portions, as is illustrated in FIG. 24B.

Next, the heater switch 114 of the operation section 112 is pushed, supplying an electric current to the heater 122 through the cable 123. The heater 122 heats the staple 118, removing the bending strain from the staple 118. Thereafter, the water-supply switch 115 of the operation section 112 is pushed, whereby the water-supplying device 117 supplies cooling water to the distal end of the insertion section 111. The staple 118 is thereby cooled and hence deformed permanently. At this time, the staple 118 is held by the anvil 125. To release the staple 118 from the anvil 125, it suffices to move the staple 118 sideways to a position where the staple slips out of the anvil 125.

Since the stapler 110 heats and cools the staple 118, thus deforming the same permanently as described above, it fasten the walls A to each other, both readily and reliably. In addition, the use of the generally M-shaped staple 118 makes it possible to suture flat body tissues together.

FIGS. 25A, 25B, and 25C show a modification of the stapler 110 according to the eighth embodiment of the invention, and explain how this stapler applies a staple 118 to stitch body walls A together. The modification differs from the stapler 110 in that a staple holder 126 is removably attached to the front of the heater 122. Both the staple 118 and the staple holder 126 are made of resin which is absorbable into, or is compatible with, body tissues.

Figure 27A:
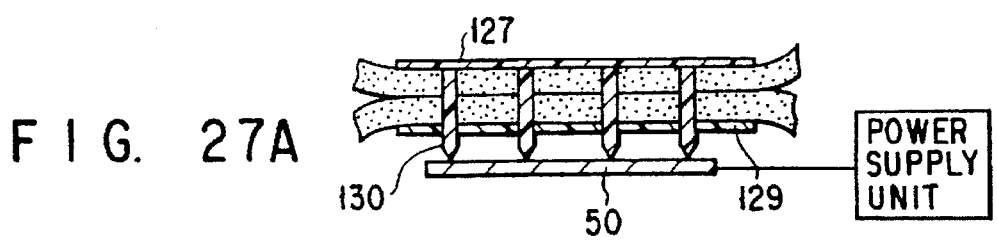
FIGS. 27A and 27B are sectional views of the staple shown in FIG. 26 and explaining how the staple fastens tow tissue layers together.
Figure 27B:
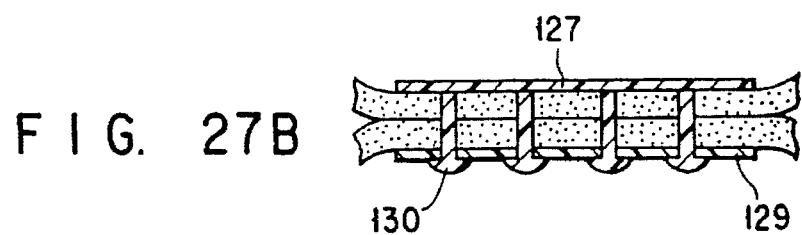

FIGS. 26 and FIGS. 27A and 27B show a staple which can be applied by the stapler 40 shown in FIG. 12. As is shown in these figures, the staple comprises a base 127, a plurality of pins 128 protruding downwards from the lower surface of the base 127, and a pin-holding plate 129 having through holes 130. The holes 130 have a diameter larger than that of the pins 128. The components of the staple 127 are all made of materials which can be absorbed into body tissues. More precisely, the pins 128 are made of material having a softening point higher than the material of the pin-holding plate 129. As is shown in FIG. 27A, a heater 50 is used to heat and thermally deform the lower ends of the pins 128.

After inserted in the through holes 130 of the pin-holding plate 129, the pins 128 of the staple 127 are fused at their tips, whereby the tissue layers clamped, as if riveted, between the base 127 and the pin-holding plate 129. The tissue layers are thereby fastened to each other steadfastly. Since the plate 129 shields the heat emanating from the heater 50, thermal damages, if any, to the body tissues can be minimized. Further, since the staple pins 128 have no projections or stepped portions, they do not damage the body tissues so much.

Figure 28:
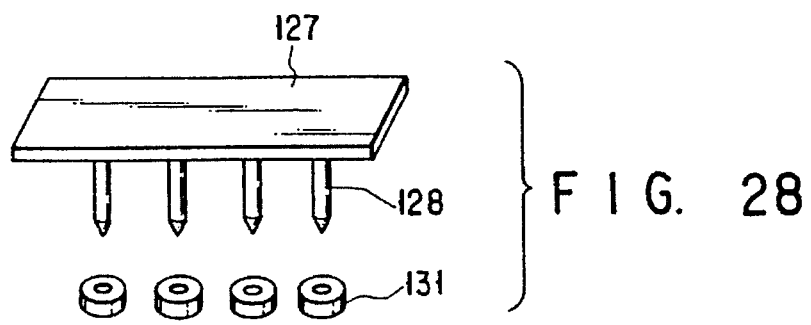
FIG. 28 is an exploded view illustrating a second modification of the staple which is applied by the stapler shown in FIG. 12.
Figure 29:
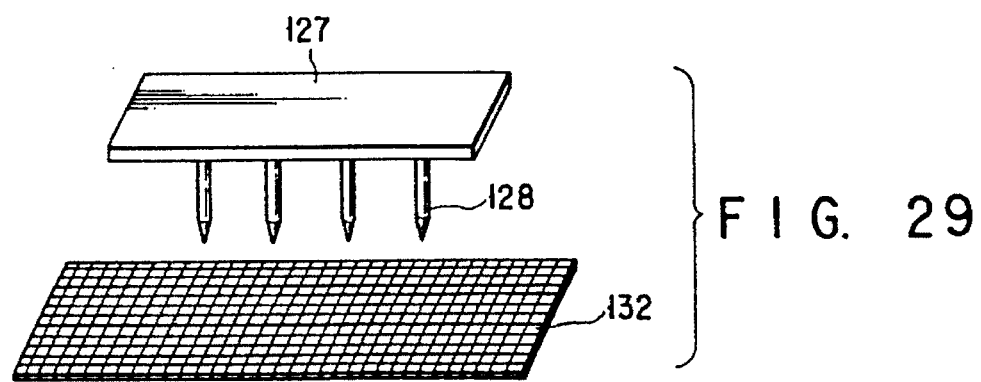
FIG. 29 is an exploded view showing a third modification of the staple which is applied by the stapler shown in FIG. 12.

The stapler 40 can apply other types of staplers which are shown in FIGS. 28 and 29. The staple shown in FIG. 28 differs from the stapler shown in FIG. 27 in that a plurality of rings 131 replace the plate 129. The staple shown in FIG. 29 differs from the stapler shown in FIG. 27 in that a meshed plate 132 having grids replaces the plate 129.

Figure 30A:
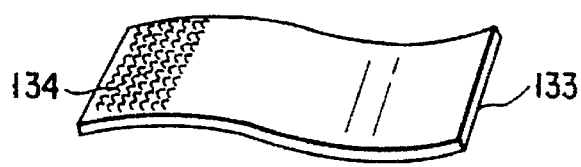
FIGS. 30A and 30B are perspective views showing a fourth modification of the stapler which is applied by the stapler.
Figure 30B:
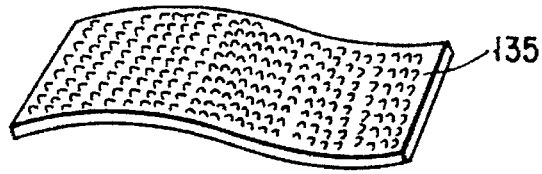

FIGS. 30A and 30B shows a staple 133 of so-called "magic tape type." The staple 133 has a number of arch-shaped projections 134 which protrude from a half of the lower side as shown in FIG. 30A, and also a number of J-shaped projections 135 protrude from the entire upper side. Each of the J-shaped projections 135 can catch one arch-shaped projection 134. The staple 133 is made of resin which can be absorbed into, or is compatible with, body tissues.

Figure 31:
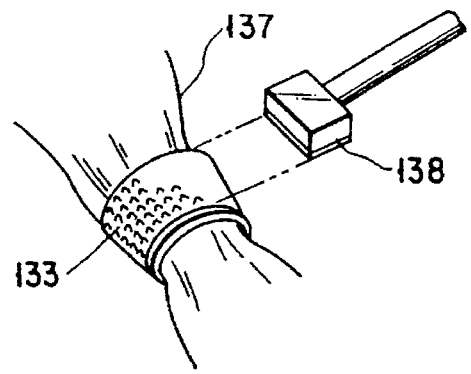
FIG. 31 is a view explaining how the stapler shown in FIGS. 30A and 30B is used to ligate a tubular organ.

How to ligate a tubular organ (e.g., a blood vessel) by using the staple 133 will be described, with reference to FIG. 31. First, the staple 133 is wound tight around the severed edge portions of a tubular organ 137, thereby tying them together. Then, a heater 138 is put in contact with the arch-shaped projections 134, fusing the projections 134 to the upper side of the staple 133, whereby the tubular organ 137 is ligated. The staple 133 wound around the tubular organ 137 is a strip having a first portion and a second portion which hold the opposing parts of the organ 137, respectively.

The magic-tape type staple 133 can be applied to ligate tubular organs of various sizes, and can adjust the tightening the organs to any desired degree.

Figure 32A:
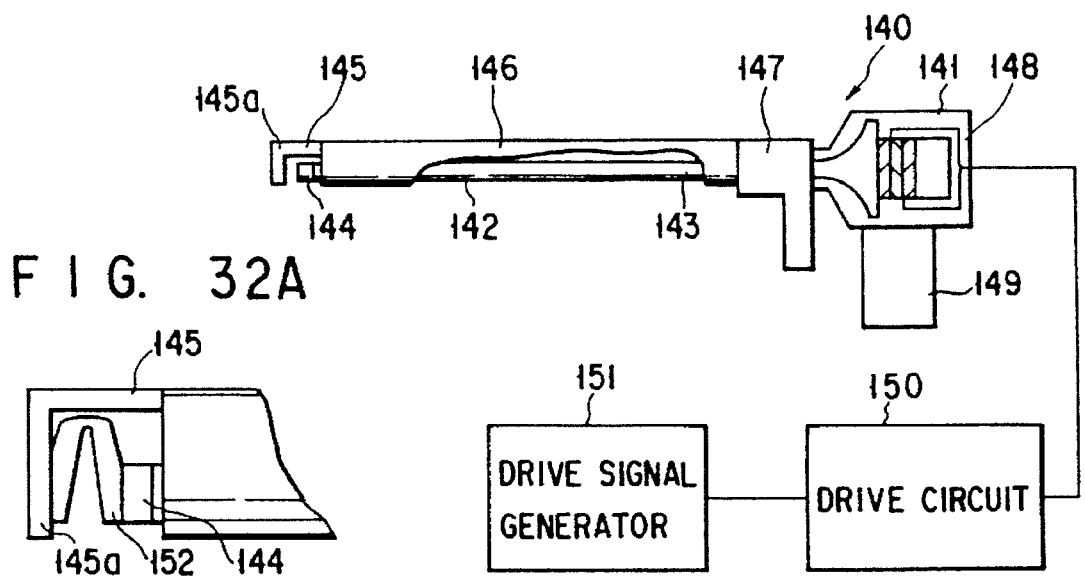
FIG. 32A is a diagram schematically showing a clip applicator which is a ninth embodiment of the present invention.
Figure 32B:
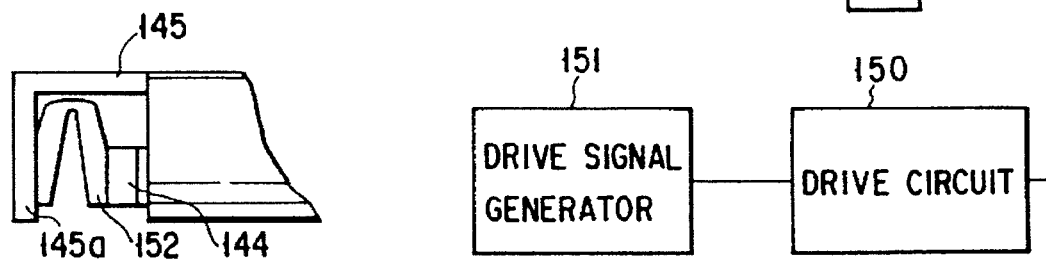
FIG. 32B is a side view of the distal end portion of the clip applicator shown in FIG. 32A.

A clip applicator 140, which is a ninth embodiment of this invention, will be described with reference to FIGS. 32A and 32B. This applicator 140 is designed to apply a clip 152 of the same type as shown in FIG. 6. The distal end of the applicator 140 contains a Langevin-type ultrasonic oscillator 141 which has a horn at its tip. Connected to the distal end of the oscillator 141 is an oscillation-transmitting member 142. The member 142 comprises an oscillation-transmitting body 143 and a tip 144. The body 143 has a threaded hole. The tip 144 has a threaded portion set in screw engagement with the threaded hole of the body 143.

An L-shaped member 145 is located near the tip 144 of the oscillation-transmitting member 142. The member 145 has a distal end portion 145a located in front of the tip 144, spaced apart therefrom by a predetermined distance. The L-shaped member 145 is connected at rear end to a support pipe 146, which in turn is fastened to a sliding member 147. The sliding member 147 is slidably mounted on the distal end portion of a case 148 containing the ultrasonic oscillator 141. The case 148 has a grip 149 at which the applicator 140 can be held by hand. The ultrasonic oscillator 141 is connected to a drive circuit 150, which is connected to a drive signal generator 151.

In operation, the drive circuit 150 amplifies a drive signal the generator 151 has output. The amplified drive signal is supplied to the ultrasonic oscillator 141. Driven by the signal, the oscillator 141 generate ultrasonic oscillation, which is applied to the oscillation-transmitting body 143 and hence to the tip 144. The body 143 has such a length that the oscillation amplitude is maximal (i.e., with the anti-node located) at the end face of the tip 144.

The applicator 140 is operated as follows, in order to apply the clip 152. First, the clip 152 is clamped between the tip 144 and the distal end portion 145a of the L-shaped member 145. Next, the sliding member 147 is slid toward the case 148, moving the portion 145a toward the tip 144. The clip 152 is thereby collapsed, with its legs contacting each other at their tips. As a result, the clip 152 constricts a tubular organ (not shown) placed between the legs with an appropriate force. In other words, the clip 152 held between the tip 144 and the L-shaped member 145 clamps the organ. In this condition, the ultrasonic oscillator 141 is driven, applying ultrasonic oscillation to the tip 144 for a predetermined time. During this time, the contacting legs of the clip 152 undergo dynamic friction, generating heat and eventually fusing to each other. As a result, the clip made of resin closes permanently, clipping the tubular body steadfastly.

A stapler 155, which is a tenth embodiment of this invention, will be described with reference to FIGS. 33, 34, 35, 36A, 36B.

Figure 33:
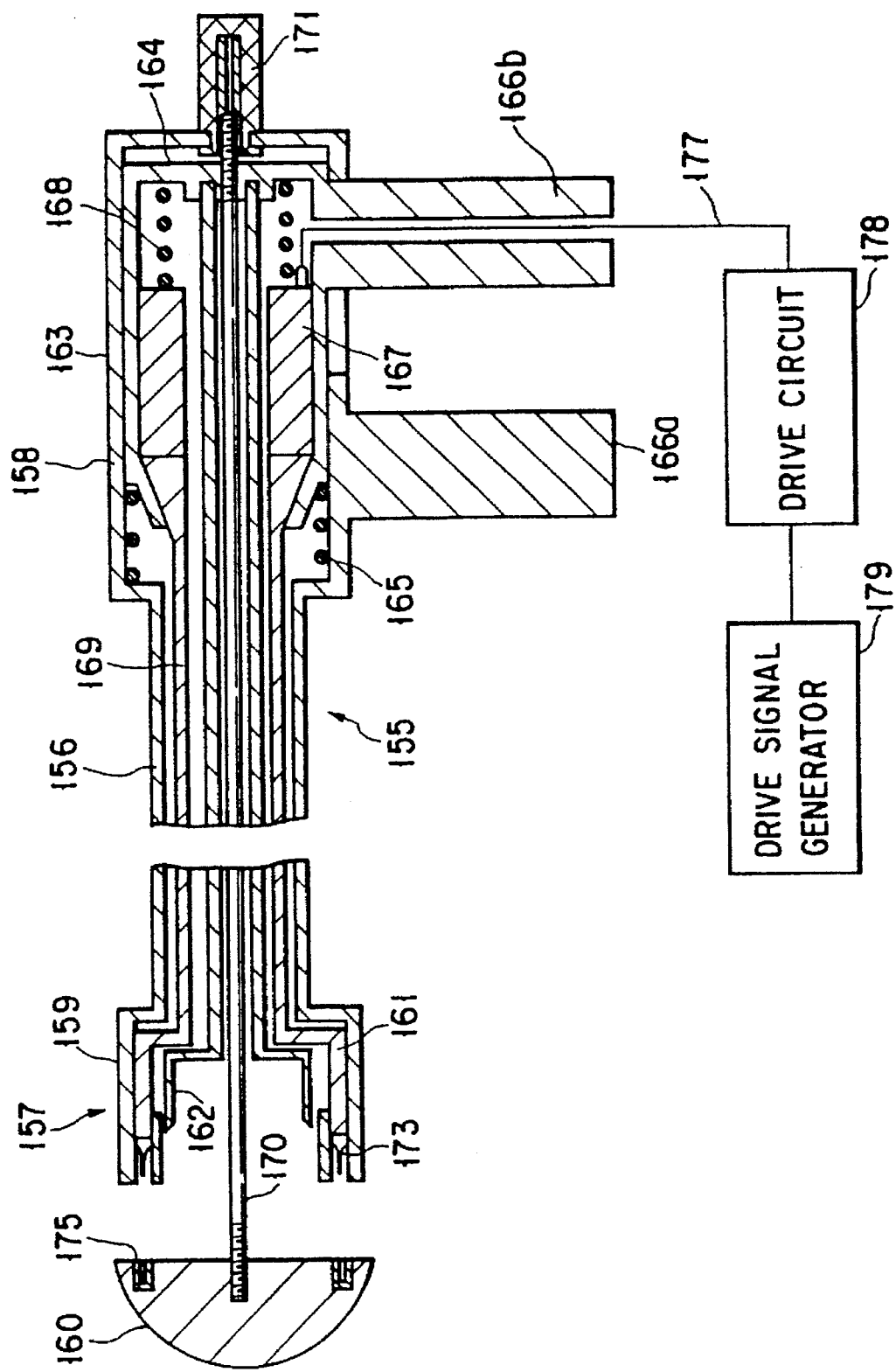
FIG. 33 is a schematic representation of a stapler which is a tenth embodiment of the present invention.

As FIG. 33 shows, this stapler 155 comprises a sheath 156 to be inserted into a tubular organ such as intestine, a stapling section 157 coupled to the distal end of the sheath 156, and an operation section 158 connected to the proximal end of the sheath 156.

Figure 34:
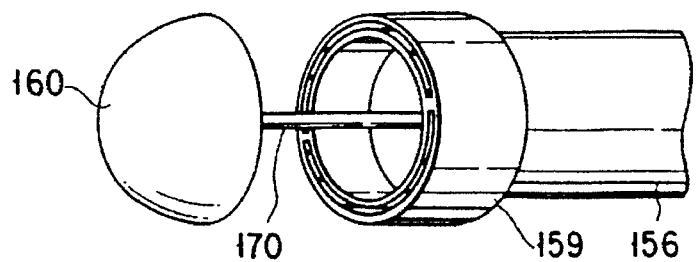
FIG. 34 is a perspective view showing the distal end portion of the stapler shown in FIG. 33.

As clearly shown in FIG. 34, the stapling section 157 comprises a hollow cylindrical housing 159 atttached to the distal end of the sheath 156, and an anvil 160 located at the front of the housing 159. As shown in FIG. 33, the housing 159 contains a staple pusher 161 and a cylindrical cutter 162, which can be moved back and forth. The staple pusher 161, which is a hollow cylinder, is used to push a first ring 173 (later described) toward the anvil 160. The cutter 162 is provided for cutting off the unnecessary portions of the tubular organ after the two severed parts of the organ have been stapled together.

Figure 35:
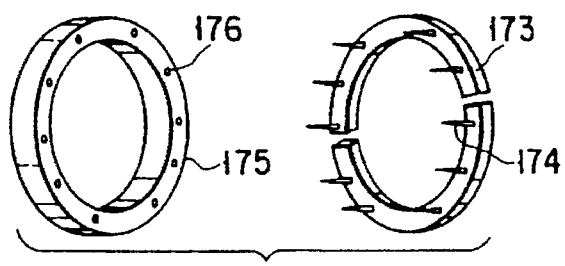
FIG. 35 is an exploded view illustrating a staple which is applied by the stapler of FIG. 33.

As is shown in FIG. 35, the staple to be applied by the stapler 155 comprises two rings 173 and 175. The first ring 173 has a plurality of styluses 174 which protrude in parallel to one another and spaced apart in the circumferential direction of the ring 173. The second ring 175 is removably held in the annular groove (not shown) cut in the back of the anvil 160. The ring 175 has as many holes 176 as the styluses 174, into which the styluses 174 will be inserted. Both rings 173 and 175 are made of resin which is absorbable absorbed into, or is compatible with, body tissues.

Referring back to FIG. 33, the operation section 158 comprises a housing 163 and a sliding member 164. The housing 163 is fixed to the sheath 156, and the sliding member 164 can move back and forth within the housing 163. A handle 166a is formed integral with the housing 163 and extending downward therefrom. Another handle 166b is formed integral with the sliding member 164 and extends downwards therefrom. Both handles 166a and 166b can be grasped so that the handle 116 be moved toward the handle 166a, thereby to slide the member 164 forward against the bias of a compression spring 165 contained in the sliding member 164.

As can be understood from FIG. 33, the sliding member 164 is a hollow member and contains an ultrasonic oscillator 167. The oscillator 167 is biased onto the inner front wall of the sliding member 164 by means of a compression spring 168. A hollow oscillation-transmitting member 169, which is a hollow cylinder, is coupled by a horn to the front end of the oscillator 167. The distal end of the member 169 is coupled to the rear end of the staple pusher 161, whereby the oscillation of the oscillator 167 is transmitted to the staple pusher 161 via the horn and the member 169. An anvil shaft 170 extends through the oscillation-transmitting member 169. The shaft 170 has a threaded end protruding from the housing 159 and set in screw engagement with a knob 171 which is rotatably connected to the rear end of the housing 159. When the knob 171 is turned in one direction and the other, the anvil shaft 170 is moved back and forth, whereby the space between the hollow cylindrical housing 159 and the anvil 160. The ultrasonic oscillator 167 is connected by a lead line 177 to an oscillator-driving circuit 178, which in turn is connected to a drive signal generator 179.

Figure 36A:
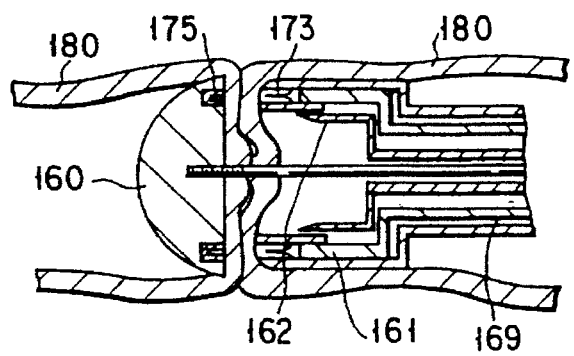
FIGS. 36A and 36B are diagrams explaining how the stapler of FIG. 33 is operated to stitch together two severed parts of a tubular organ.

The stapler 155, thus constructed, is operated as follows, to apply the staple shown in FIG. 35. First, the knob 171 is turned in a prescribed direction, moving the anvil 160 toward the hollow cylindrical housing 159, thereby clamping the abutting ends of two severed parts of a tubular organs 180 between the housing 159 and the anvil 160 as is shown in FIG. 36A. Then, the handles 166a and 166b are gripped, moving the handle 166b and hence sliding the member 164 forward. As a result, the first ring 173 of the staple is pushed out of the hollow cylindrical housing 159, whereby the styluses 174 of the first ring 173 pierce the abutting walls of the severed parts of a tubular organ 180 and fit into the holes 176 of the second ring 175. Thus, the severed parts of the organ 180 are fastened together.

Figure 36B:
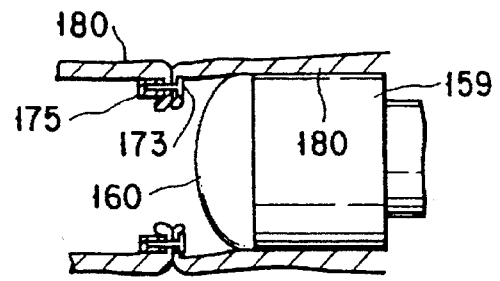

Next, the ultrasonic oscillator 167 is driven, generating ultrasonic oscillation. The oscillation-transmitting member 169 transmits the oscillation to the staple pusher 161 and hence to the first ring 173. The styluses 174 of the first ring 173, which are inserted in the holes 176 of the second ring 175, undergo dynamic friction with the second ring 175. The styluses 174 are thereby heated and fuse, whereby the rings 173 and 175 are connected to each other. Thereafter, the handle 166b is further pulled toward the handle 166a, the spring 168 is compressed, thrusting the cylindrical cutter 162 forward. As a result, the cutter 162 cuts off the unnecessary portions of the walls of the severed parts of the tubular organ 180, as is illustrated in FIG. 36B.

As described above, both rings 173 and 175 of the staple are oscillated at an ultrasonic frequency in the stapler 155 and fuse to each other by virtue of the heat generated by the dynamic friction between them. The stapler 155 can, therefore, achieve reliable suture of a tubular organ.

Figure 37:
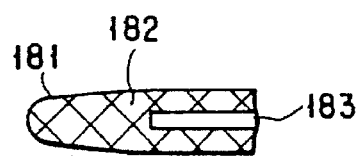
FIG. 37 is a plan view showing one of the two jaws of a clip applicator according to an eleventh embodiment of the invention.
Figure 38:
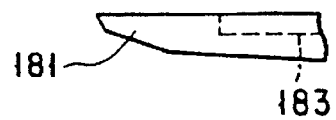
FIG. 38 is a side view showing the jaw shown in FIG. 37.

FIGS. 37 and 38 show one of jaws 181 of a clip applicator which is an eleventh embodiment of the present invention. The clip applicator has a pair of jaws 181 for holding a clip between them. Each jaw 181 has a clip-holding surface which has of a stylus-holding section 182 and a clip-holding groove 183. The stylus-holding section 182 comprises a net-shaped projections made of tungsten carbide.

Figure 39A:
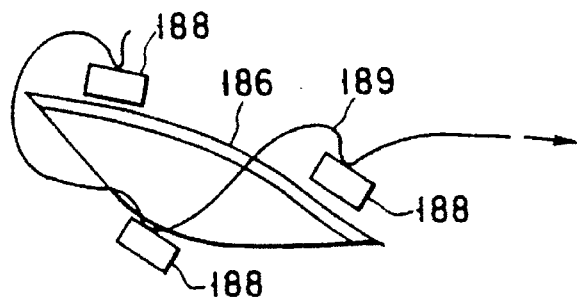
FIGS. 39A and 39B are diagrams explaining how a clip applicator according to a twelfth embodiment of the invention apply a plurality of clips, gathering and stitching together the tissues.
Figure 39B:
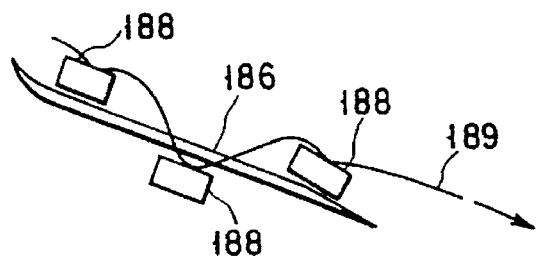

FIGS. 39A and 39B explain how a clip applicator according to a twelfth embodiment of the invention apply a plurality of clips 188 in order to gather and stitch together the tissues on the sides of a wound. As shown in FIG. 39A, the clips 188 loosely connected by a thread 189 are fixed to both sides of the wound in staggered fashion. Then, the thread is pulled, moving the clips 188 on one side of the would toward those on the other wide thereof as shown in FIG. 39B. As a result, the tissues on the sides of the wound are gathered and stitched to each other.

A clip applicator 191, which is a thirteenth embodiment of the present invention, will be described with reference to FIGS. 40, 41 and 42 and FIGS. 43A, 43B and 43C.

Figure 40:
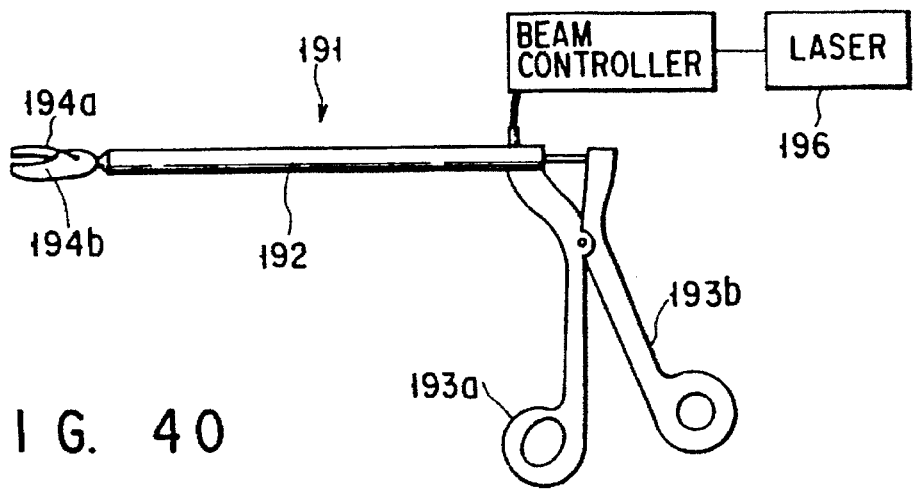
FIG. 40 is a schematic representation of a clip applicator which is a thirteenth embodiment of the present invention.

As can be understood from FIG. 40, the clip applicator 191 comprises a sheath 192, two handles 193a an 193b both connected to the proximal end of the sheath 192, and a pair of jaws 194a and 194b connected to the distal end of the sheath 192. The sheath 192 can be inserted into a body cavity, guided through a tubular instrument such as a trocar. The handle 193a is fixed to the sheath 192, and the handle 193b is rotatably coupled to the middle portion of the fixed handle 193a. The lower jaws 194b is fastened to the distal end of the sheath 192, and the upper jaw 194a is rotatably coupled to the lower jaw 194b. A connecting rod extends through the sheath 192, connecting the upper jaw 194a to the upper end of the rotatable handle 193b. Hence, when the rotatable handle 193b is moved toward and away from the fixed handle 193a, the rod moves the upper jaw 194a into its open position and into its close position.

Figure 41:
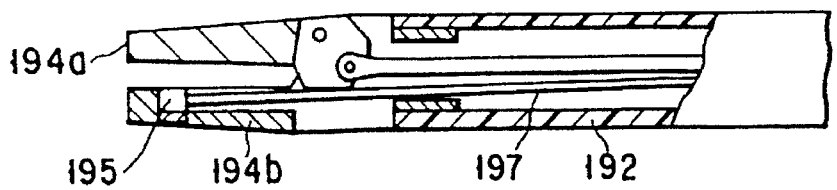
FIG. 41 is a partly sectional side view showing the distal end portion of the clip applicator shown in FIG. 40.

As is shown in FIG. 41, the lower jaw 194b has a hole 195 opening in the side opposing the upper jaw 194a. As shown in FIG. 40, a laser 196 and a beam controller are located outside the clip applicator 191. The laser 196 is connected to the beam controller. An optical fiber 197 extends from the beam controller to the hole hole 195, passing through the sheath 192.

Figure 42:
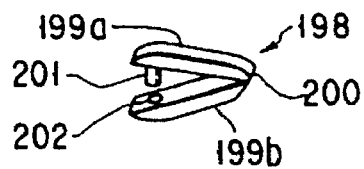
FIG. 42 is a perspective view illustrating a clip which the applicator of FIG. 40 is to apply.

FIG. 42 shows a clip 198 which the applicator 191 applies. The clip 198 is made of resin, having an upper leg 199a and a lower leg 199b which are connected to each other at a hinge portion 200. The upper leg 199a has a pin 201 protruding toward the lower leg 199b. The lower leg 199b has a through hole 202 so positioned as to received the pin 201 when the legs 199a and 199b abut on each other.

Figures 43A, 43B, 43C:
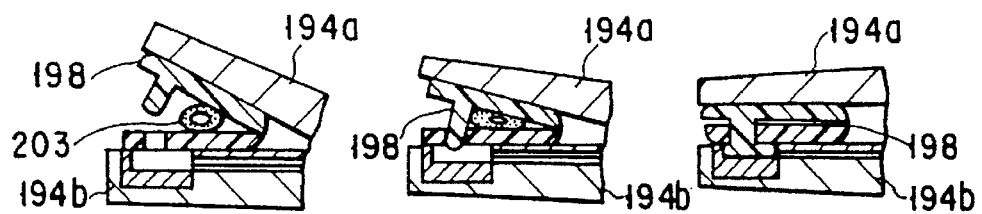
FIGS. 43A, 43B, and 43C are diagrams explaining how the clip applicator is used to ligate a tubular organ.

The clip applicator 191 is manipulated as follows, in order to apply the clip 198 to ligate a tubular organ. The clip 198 is held between the jaws 194a and 194b as shown in FIG. 43A, and a tubular organ 203 is placed between the legs 199a and 199b of the clip 198. Next, as shown in FIG. 43B, the handles 193a and 193b are gripped, moving the handle 193b toward the handle 193a, whereby putting the upper jaw 194a into the close position. As shown in FIG. 43C, the clip 198 is closed, with its pin 201 inserted into the hole 202. In this condition, a laser beam is applied from the laser 196 into the hole 195 of the lower jaw 194b through the beam controller and the optical fiber 197. The thermal energy of the beam melts that portion of the pin 201 which is inserted in the hole 202, fusing the same to the lower side of the lower leg 199b.

Once the lower end of the pin 201 has been thus fused to the lower side of the leg 199b, the clip 198 does not release the tubular organ 203. Thus, the clip applicator 191 can ligate tubular organs with reliability.

The clip applicator 191 is of the type designed to apply one clip at a time. Instead, it may be of the type which can apply a plurality of clips at a time.

A stapler 210 according to a fourteenth embodiment of the invention will be described, with reference to FIGS. 44, 45, and 46.

Figure 44:
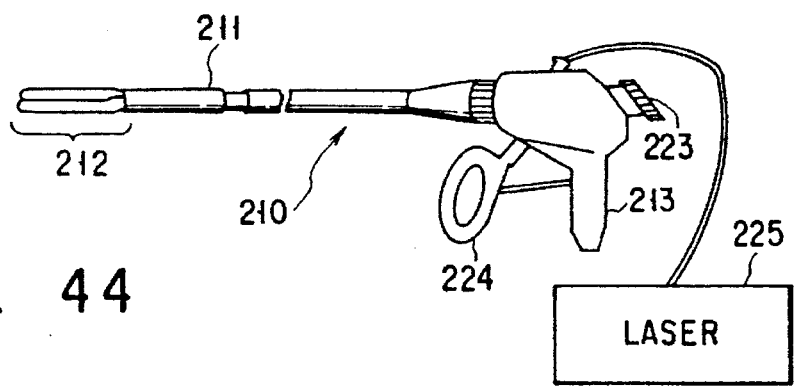
FIG. 44 is a side view of a stapler according to a fourteenth embodiment of the present invention.

As is evident from FIG. 44, the stapler 210 comprises an insertion section 211, a stapling section 212 attached to the distal end of the insertion section 211, and an operation section 213 fixed to the proximal end of the insertion section 211.

Figure 45:
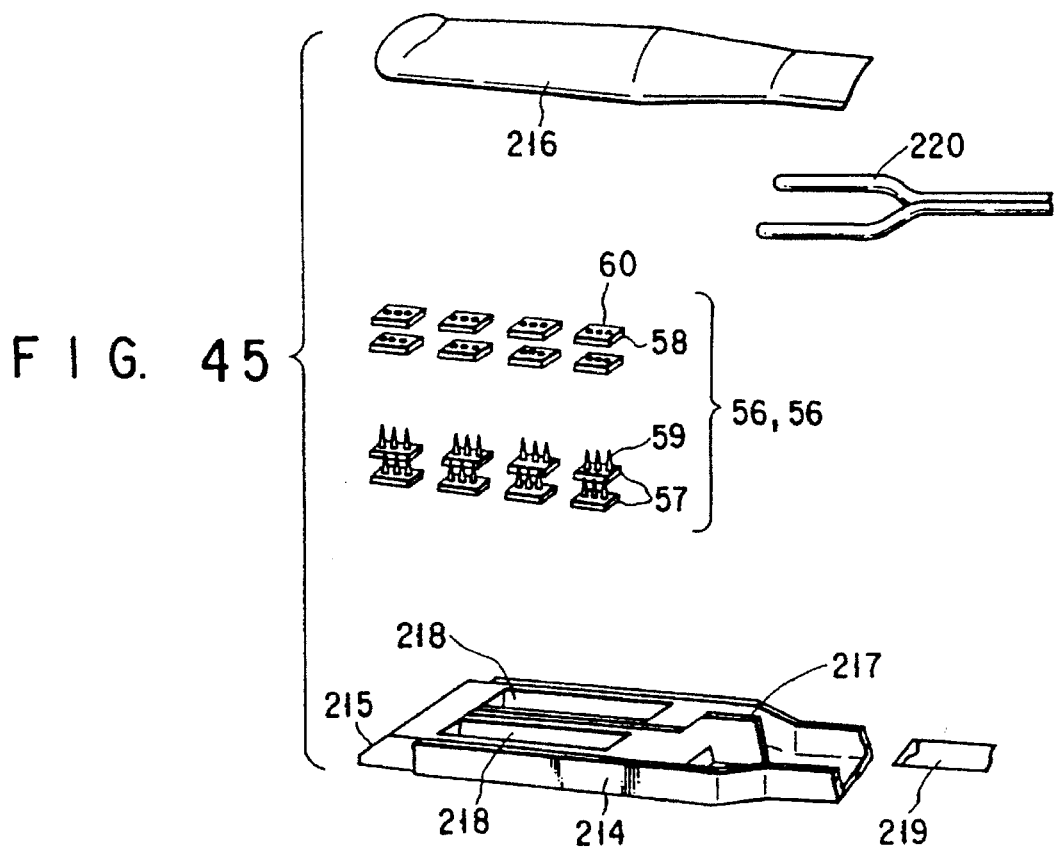
FIG. 45 is an exploded view showing the distal end portion of the stapler shown in FIG. 44.

As FIG. 45 shows, the stapling section 212 comprises a casing 214, a cartridge 215, and an anvil 216. The casing 214 is generally a top-opening rectangular box and secured to the distal end of the insertion section 211. The cartridge 215 is removably contained in the casing 214. The anvil 216 is hinged at its read end to the rear end of the casing 214 and can therefore be rotated to an open position and a closed position; it is normally in the closed position, covering the top (i.e., staple-holding surface) of the casing 214. A knife-guiding groove 217 is formed in the top surface of the casing 214, extending along the axis of the casing 214 for guiding a knife 219 used for sever body tissues. Also formed in the top surface of the casing 214 are two rectangular recesses 218 located on the sides of the groove 217, for holding the bases 57 of staples 56. The staple bases 57 are placed in each recess 218. The staples 56 are identical to those shown in FIG. 12, and will not described here again.

Figure 46A:
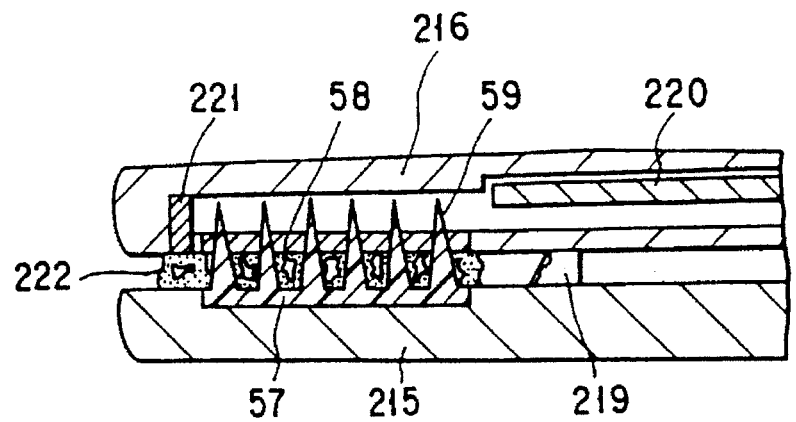
FIGS. 46A and 46B are cross-sectional view showing the distal end portions and explaining how the stapler is manipulated to apply a plurality of staples.
Figure 46B:
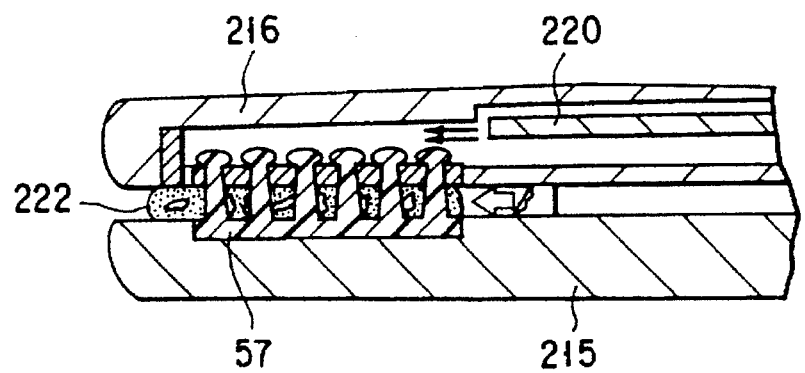

The anvil 216 contains a laser probe 220 and a heat-resistant member 221. The laser probe 220 is used to heat and deform deforming the tips of the pins 59 of each staple 56. As shown in FIG. 46A and 46B, the heat-resistant member 221 is positioned, opposing the tip of the laser probe 220. The anvil 216 also contains staple covers 58.

Referring to FIG. 44 again, the operation section 213 has a handle 223 for opening and closing the anvil 216, and a firing handle 224 for applying a laser beam to the probe 220. A laser 225 is connected to the operation section 213.

The stapler 210 is manipulated in the following way. First, the stapling section 212 is positioned such that the body tissues 222 are placed between the cartridge 215 and the anvil 216. Next, the handle 223 is operated, rotating the anvil 216 to the closed position and, hence, clamping the body tissues 222. The pins 59 of each staple 56 pierce the tissues 222 and slip into the holes 60 of the cover 58 and protrude from the cover 58, as is illustrated in FIG. 46A. The firing handle 224 is pulled, applying a laser beam from the laser 225 to the laser probe 220 and hence to the tips of pins 59. The pins 59 are heated and fused onto the upper surface of the cover 58 as is shown in FIG. 46B. As a result, the staples 56 fasten the body tissues 222 together—as steadfastly as in the staplers shown in FIGS. 11 and 19.

A clip applicator 230, which is a fifteenth embodiment of the invention, will be described with reference to FIGS. 47 to 55.

Figure 47:
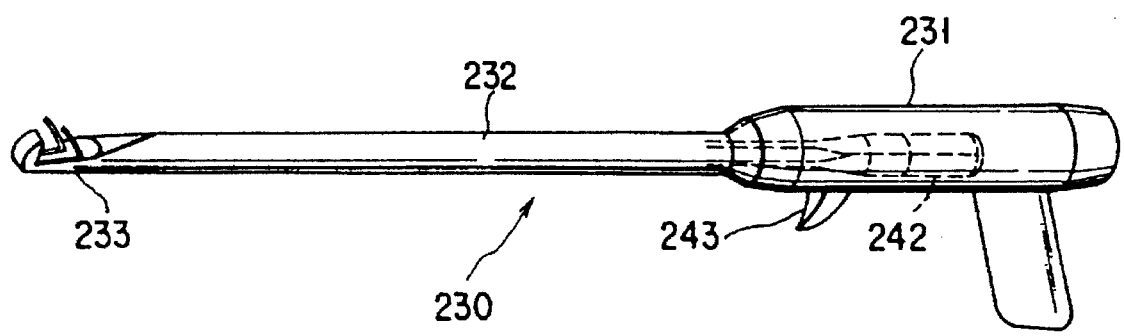
FIG. 47 is a perspective view showing a clip applicator which is a fifteenth embodiment of the present invention.
Figure 48:
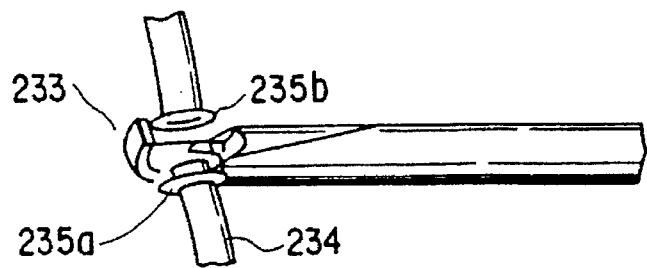
FIG. 48 is a perspective view showing a clip applicator which is a fifteenth embodiment of the present invention.

As shown in FIG. 47, the clip applicator 230 comprises an operation section 231, an insertion tube 232 extending from the distal end of the operation section 231, and a clip-applying section 233 connected to the distal end of the tube 232. The tube 232 is to be inserted into a body cavity, and the clip-applying section 233 is designed to apply two clips 235a and 235b to ligate a tubular organ 234 such as a blood vessel and subsequently sever the organ 234, as is illustrated in FIG. 48.

Figure 49:
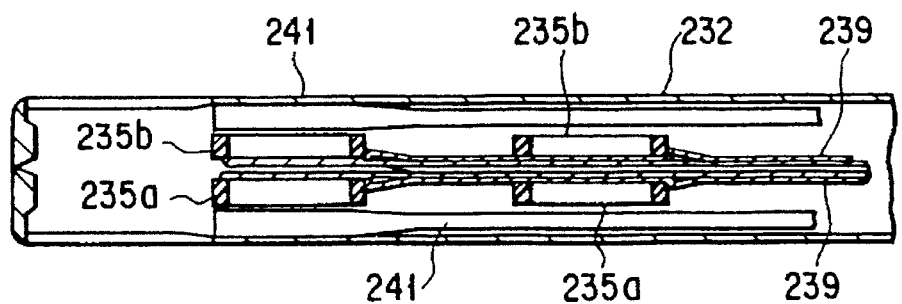
FIG. 49 is a sectional view showing the distal end portion of the clip applicator shown in FIG. 48.
Figure 50:
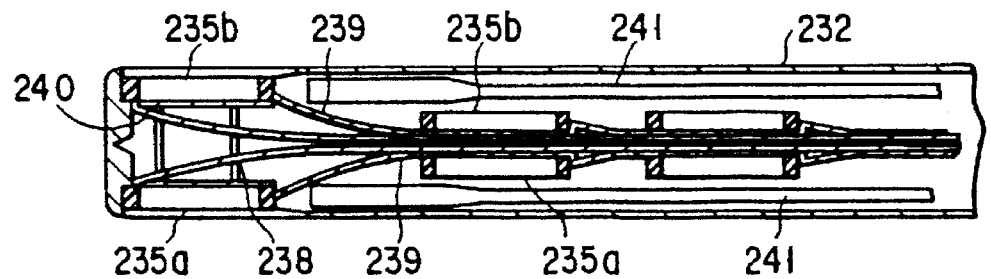
FIG. 50 is a diagram explaining how to manipulate the clip applicator of FIG. 48.
Figure 51:
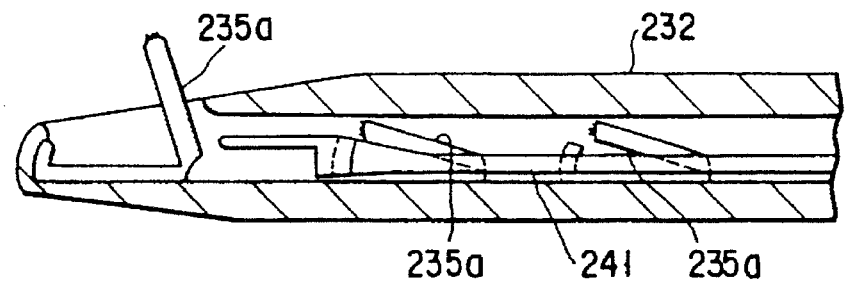
FIG. 51 is also a diagram explaining how to manipulate the clip applicator of FIG. 48.

Both clips 235a and 235b are made of resin which can be absorbed into body tissues. As shown in FIG. 52, each clip has a sawtoothed portion 236 at one end, and a holder portion 237 at the other end. The holder portion 237 is designed to hold the sawtoothed portion 236. The clips 235a and 235b are connected by two strips 238 of adhesive tape. As shown in FIG. 49, the clips 235a and 235b are contained in the insertion tube 232 and can be pushed to the clip-applying section 233 by means of a pair of clip-pushing springs 239 which extend through the insertion tube 232. Another pair of springs 240 extend through the tube 232, between the clip-pushing springs 239. When the springs 240 are thrust to the clip-applying section 233, their distal end portions spread sideways by their own bias, moving two clips 235a and 235b already pushed into the clip-applying section 233 as is illustrated in FIG. 50. As a result, the clips 235a and 235b are placed at positions where they oppose the distal ends of clip-holders 241 located within the insertion tube 232.

The clip holders 241 are connected to an ultrasonic oscillator 242 which is incorporated in the operation section 231 as shown in FIG. 47, so that the ultrasonic oscillation generated by the oscillator 242 may be transmitted to the clip holders 241. The ultrasonic oscillator 242 can be moved back and forth in the operation section 231 when a handle 243 (FIG. 47) is operated. More precisely, when the handle 243 is squeezed, the oscillator 242 is pushed forward. As shown in FIG. 55, a knife 245 extends through the insertion tube 232 and can slide along the axis of the tube 232 for cutting the tubular organ 234 and the strips 238 of adhesive tape.

In operation, the clips 235a and 235b pushed into the clip-applying section 233 are closed by operating the clip holders 241. This done, the ultrasonic oscillator 242 is energized, generating ultrasonic oscillation. The clip holders 241 transmits the oscillation to the closed clips 235a and 235b. By virtue of the ultrasonic oscillation, heat is generated between the sawtoothed portion 236 and holder portion 237 of each clip which are in frictional contact. The portions 236 and 237 of the clip are thereby fused together. As a result, the clips 235a and 235b would not open, reliably clamping the tubular organ 234.

Since the sawtoothed portion 236 and holder portion 237 of each clip are heated by ultrasonic oscillation, the remaining parts of the clip are not heated so much as to lose their rigidity.

The legs of the clip hitherto been used to ligate a tubular organ by mechanical means (e.g., latches) needs to have a large contacting surfaces to ensure reliable ligation of the organ. Inevitably it large and thick as a whole; it requires a large incision for penetration into a body cavity and is difficult to handle. By contrast, the clips 235a and 235b are sufficiently small since the legs of each clip are fastened to each other by ultrasonic oscillator, not by any mechanical means.

Figure 56:
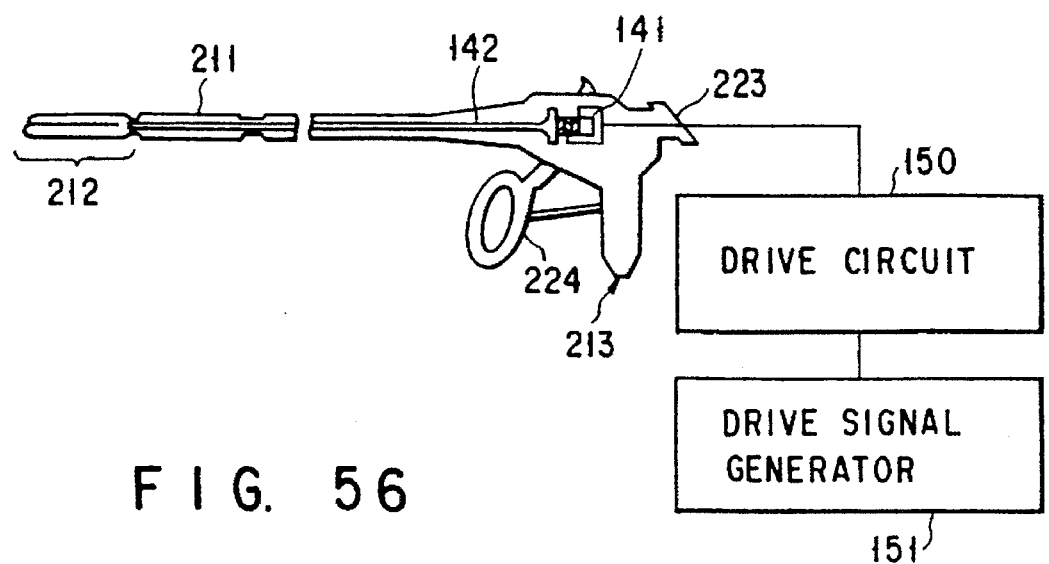
FIG. 56 is a schematic representation of a stapler which is a sixteenth embodiment of this invention.
Figure 57:
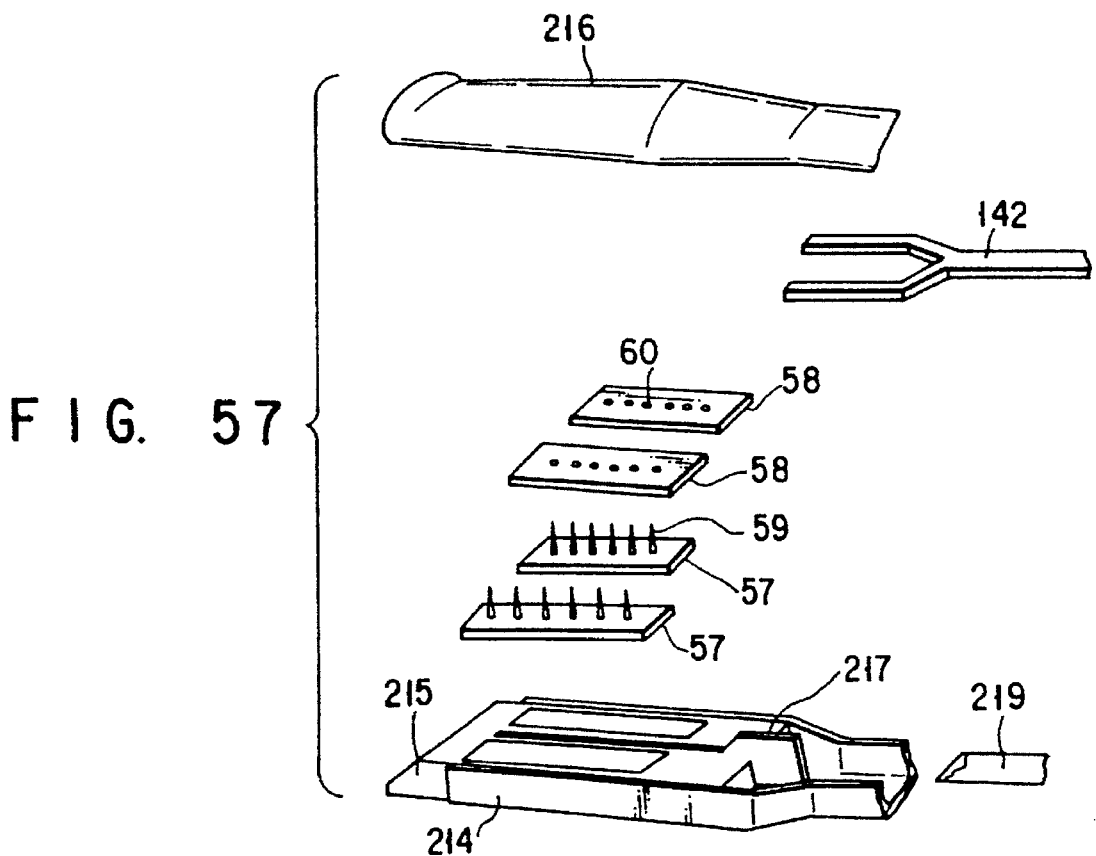
FIG. 57 is an exploded view showing the distal end portion of the stapler shown in FIG. 56.

A stapler, which is a sixteenth embodiment of the invention, will be described with reference to FIGS. 56, 57, and 58. This stapler is identical to the stapler 210 shown in FIGS. 44 and 45, except that the laser probe 220 is replaced by the ultrasonic oscillator 141 and the oscillation-transmitting member 142, both shown in FIG. 32, in order to fasten the staple bases 57 and the staple covers 58 by means of ultrasonic oscillation. Once the base 57 and corresponding cover 58 of each staple 56 are fused together by virtue of ultrasonic oscillation as shown in FIG. 58, the staple 56 keeps holding body tissues 222 in stead fast connection.

Another clip applicator, which is a seventeenth embodiment of the present invention, will be described with reference to FIGS. 59, 60, and 61.

As can be seen from FIG. 59, the clip applicator comprises an operation section 250 and an insertion section 251 extending from the distal end of the operation section 250. The operation section 250 contains an ultrasonic oscillator 252 and a horn 253, and has a handle 254 and a grip 255. An oscillation-transmitting member 256 extends forward from the horn 253 through the insertion section 251. The member 256 has an oscillating tip 257. A clip holder 258 is inserted in the distal end of the insertion section 251 and can be moved along the axis of the section 251 as the handle 254 is operated. The handle 254, insertion section 251 and clip holder 258 together comprise an operating means. The ultrasonic oscillator 252 is connected to a drive circuit 259, which in turn is connected to a drive signal generator 260 to serve as a heating means.

FIG. 61 shows a clip 261 which the applicator applies to ligate a body organ. The clip 261 is a molding made of thermoplastic resin. It comprises a pair of legs 262a and 262b (first and second support means, respectively) and a hinge 263 connecting the legs 262a and 262b at one end. The hinge 263 serves as a coupling means for coupling the legs 262a and 262b together. A plurality of tiny projections (pins) 264 protrude from the opposing sides of the tips of the legs 262a and 262b. The projections 264 and portions of said clip 261 comprise a displacement-preventing means, as is described hereinbelow. The leg 262a is thinner than the leg 262b and can be bent more easily.

As is shown in FIG. 60, the clip holder 258 has an L-shaped anvil 265 (holding means) which opposes the oscillating tip 257 of the oscillation-transmitting member 256. The clip 261 is held, with the legs 262a and 262b abutting on the oscillating tip 257 and the anvil (holding means) 265, respectively. The oscillation-transmitting member 256 is held in a retreated position by a spring (not shown), and the anvil 265 can be moved backwards by operating the handle 254.

The clip applicator shown in FIG. 59 is operated in the following way. First, the clip 261 is held between the anvil 265 and the oscillating tip 257 of the member 256 as is shown in FIG. 60. Then, body tissues to be fastened together are moved into the gap between the legs 262a and 262b of the clip 261, while being observed through an endoscope. Next, the handle 254 is pulled, moving the anvil 265 backwards. The clip 261 is thereby closed, clamping the tissues. In this condition, the ultrasonic oscillator 252 is driven, generating ultrasonic oscillation. The oscillation-transmitting 256 transmits the oscillation to the clip 261. The projections 264 of the leg 262a and the projections 264 of the leg 262b, which abut in point contact, are oscillated and fused together, whereby the legs 262a and 262b are permanently connected to each other (prevented from being relatively displaced).

Due to the point contact between the projections 264 of the leg 262a and those of the leg 262b, heat is generated concentratedly at the tips of the projections 264, whereby the (or pins) 264 can be fused within a short time. Even if the tissues are wet with body fluid such as blood, the projections 264 reliably abut on one another, the legs 262a and 262b can be fastened together readily and steadfastly.

FIG. 62 shows a clip 267 which is an eighteenth embodiment of the present invention. The clip 267 comprises a pair of legs 268a and 268b and a hinge 269 connecting the legs 268a and 268b at one end. All components of the clip 267 are formed integral, made of resin. Those portions 270 of the legs 268a and 268b, which extend between the hinge 269 and the free ends of the legs 268a and 268b, are made of foamed resin or porous resin. The mutually opposing sides of the tips of the legs 268a and 268b serve as fusing surfaces 271. A rectangular fuse 272 is mounted on the surface 271 of the leg 268a. The leg 268b has a rectangular recess 273 formed in that side of its tip which faces away from the fusing surface 271. The recess 273 serves to transmit ultrasonic oscillation readily to the leg 268b.

When the clip 267 is held and closed at the distal end of the applicator shown in FIG. 59 (i.e., the seventeenth embodiment) and then subjected ultrasonic oscillation, the fuse 272 is fused to the fusing surface 271 of the legs 268a and 268b, whereby the legs 268a and 268b are deformed and fastened together firmly. The ultrasonic oscillation applied to the recess 273 is not well transmitted to the portions 270 of the clip 267 because the portions 270 are less dense than any other portions. Hence, the portions 270 generate far less heat, if any, scarcely affecting the tissues clamped between the legs 268a and 268b with oscillation or heat. Not the entire portions 270, but only the surface regions thereof may be made of foamed resin or porous resin. Alternatively, a sponge-like resin layer may be bonded to the inner surface of each leg.

FIG. 63 shows a clip 275 which is a nineteenth embodiment of the present invention. The clip 275 comprises a pair of legs 276a and 276b and a hinge 277 coupling the legs 276a and 276b at one end. All components of the clip 275 are formed integral, made of thermoplastic resin. The leg 276a has a raised portion 278 on the inner surface of its free end, whereas the leg 276b has a recessed portion 279 formed in the inner surface of its free end. The leg 276b has a rectangular recess 280 formed in the outer side of its free-end portion. When to be used, the clip 275 is held in the distal end of the applicator shown in FIG. 59 (i.e., the seventeenth embodiment), with the oscillating tip 257 of the member 256 abutting on the bottom of the rectangular recess 280. Once the clip 275 is closed, clamping tissues between the legs 276a and 276b, the raised portion 278 of the leg 276a fits into the recessed portion 278 of the leg 276b. The legs 276a and 276b are thereby prevented from displacing sideways from each other. This helps to shorten the time required for fusing the free ends of the legs 276a and 276b together.

FIG. 64 shows a clip 281 which is a twentieth embodiment of this invention. Like those shown in FIGS. 61, 62, and 63, the clip 281 comprises a pair of legs 282a and 282b and a hinge 283 coupling the legs 282a and 282b at one end, and all of its components are formed integral and made of thermoplastic resin. The leg 282a has a projection 284 protruding from that part of its inner surface which is close to the hinge 283. To ligate tissues together, the clip 281 is closed, holding the tissues between the legs 282a and 282b, with the projection 284 abutting on the inner surface of the leg 282b. In this condition, ultrasonic oscillation is applied to the clip 281. The projection 284 is thereby melted and fused to the leg 282b, whereby the legs 282a and 282b are fastened to each other, clamping the tissues steadfastly. As can be understood from FIG. 64, the middle portion of the leg 282a is gently curved away from the leg 282b.

Since no projections protrude from the free-end portion of the leg 282a or 282b, body tissues can be smoothly guided into the gap between the legs 282a and 282b; the projection 284, located near the hinge 283, does not impede the guiding of the tissues. Further, since the middle portion of the leg 282a is gently curved away from the leg 282b, the tissues clamped between the legs 282a and 282b do not hinder the fusing of the projection 284. The clip 281 can be applied to fasten flat tissues together, too.

A twenty-first embodiment of the present invention will be described, with reference to FIG. 65, FIGS. 66A, 66B and 66C, and FIG. 67.

FIG. 65 shows a clip 290 used in this embodiment. Like those shown in FIGS. 61, 62, 63, and 64, the clip 290 comprises a pair of legs 291a and 291b and a hinge 292 coupling the legs 291a and 291b at one end, and all of its components are formed integral and made of thermoplastic resin. The clip 290 has two styluses 293 and 294 protruding from the inner surface of the leg 191b and located at the middle and the free-end portions of the leg 291b, respectively. The stylus 293 is shorter than the stylus 294. The leg 291b has a rectangular recess 295 formed in the outer side of the free-end portion, for efficiently transmitting ultrasonic oscillation to the leg 291b.

Figure 67:
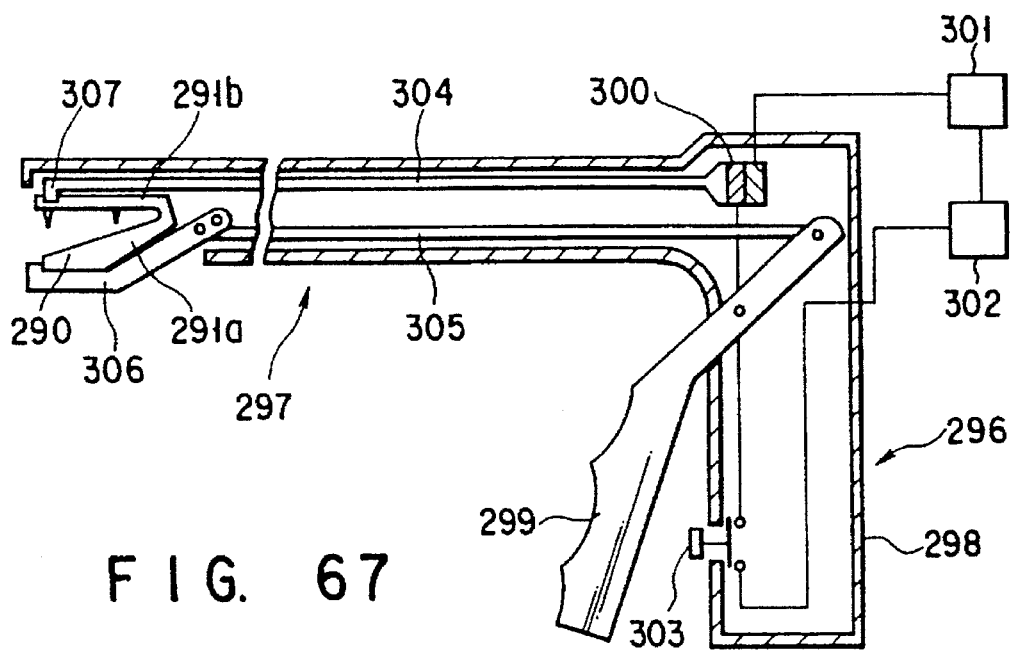
FIG. 67 is a sectional side view showing the applicator which is the twenty-first embodiment of the invention.

FIG. 67 shows an ultrasonic clip applicator designed to apply the clip 290. As is shown in the figure, the applicator comprises an operation section 296 and an insertion section 297. The operation section 296 comprises a grip 298 and a handle 299 rotatably connected to the grip 298. The grip 298 contains an ultrasonic oscillator 300. A push-button switch 303 consisting a push button (i.e., movable contact) and two stationary contacts. One stationary contact is electrically connected to the oscillator 300, which in turn is connected to a drive circuit 301 provided out side the grip 298. The other stationary contact is electrically connected to an oscillation circuit 302, which is located outside the grip 298 and connected to the drive circuit 301.

The insertion section 297 contains a member 304 for transmitting ultrasonic oscillation and a link 305 for opening and closing a jaw 306. The link 305 has its proximal end connected to the handle 299 and its distal end coupled to the rear end of the jaw 306. The jaw 306 is rotatably coupled to the distal end of the insertion section 297. The oscillation-transmitting member 304 has an oscillating tip 307.

Figures 66A, 66B, 66C:
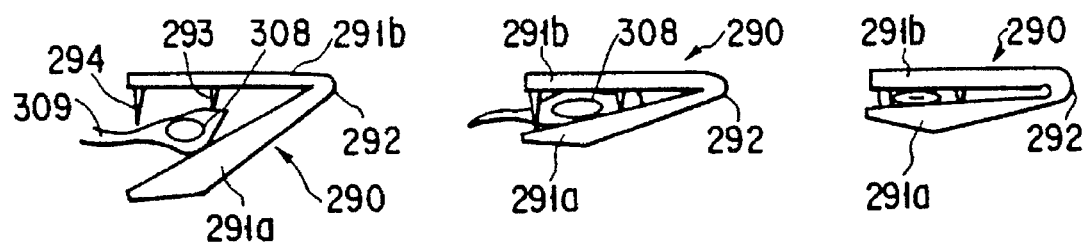
FIGS. 66A, 66B, and 66C are diagrams explaining how to apply the clip of FIG. 65 to ligate a tubular organ.

The clip applicator is manipulated as follows to apply the clip 290 in the following way. First, the clip 290 is held between the jaw 306 and the oscillating tip 307 as is shown in FIG. 67. Then, as shown in FIG. 66A, a tubular organ 308 (e.g., a blood vessel) is positioned in, the gap between the legs 291a and 291b of the clip 290. Thereafter, the handle 299 is squeezed, rotating the jaw 306 and subsequently closing the clip 290 as shown in FIG. 66B. The tubular organ 308 is thereby clamped and collapsed between the legs 291a and 291b. Then, the push-button switch 303 on the grip 298 is pushed, driving the ultrasonic oscillator 300. The oscillator 300 generates ultrasonic oscillation, which is transmitted to the clip 290 by the oscillation-transmitting member 304.

The styluses 293 and 294, which pierce a layer of fat or the like, if any, and abut on the inner surface of the leg 291b, are fused at their tips, fixing the leg 291a to the leg 291b. Hence, the clip 290 is deformed in its closed state, ligating the tubular organ 308. Both styluses 293 and 294 can easily pierce the organ 308 by virtue of the ultrasonic oscillation applied to them.

Thus, even if some tissues have not been separated from the tubular organ 308, the clip 290 can reliably ligate the organ 308. Since the styluses 293 and 294 bite into the organ 308 as the clip 290 is closed by rotating the jaw 306, that portion of the organ 308 which should be ligated is not displaced from the clip 290.

Figure 68:
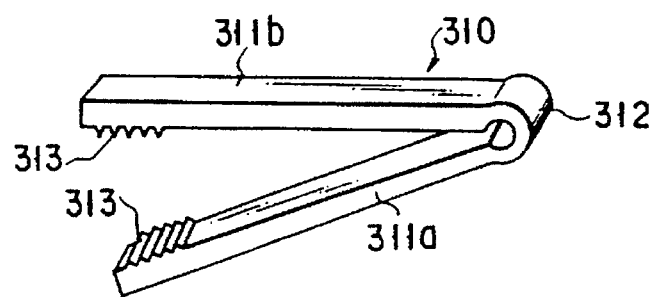
FIG. 68 is a perspective view showing a clip which is a twenty-second embodiment of the present invention.

FIG. 68 shows a clip 310 which is a twenty-second embodiment of the present invention. The clip 310 comprises a pair of legs 311a and 311b and a hinge 312 connecting the legs 311a and 311b at one end. All components of the clip 310 are formed integral and made of thermoplastic resin. Each leg has a serration 313 on the inner surface of its free-end portion. The serration 313 serves as fusing surface. The clip 310 is applied in the same way as the clips shown in FIGS. 61 to 65. The serrations 313 formed on the abutting end portions of the legs 311a and 311b can be readily fused together when ultrasonic oscillation is applied to the clip 310. The legs 311a and 311b can therefore be fastened together, creating a sufficient clamping or ligation force.

Figure 69:
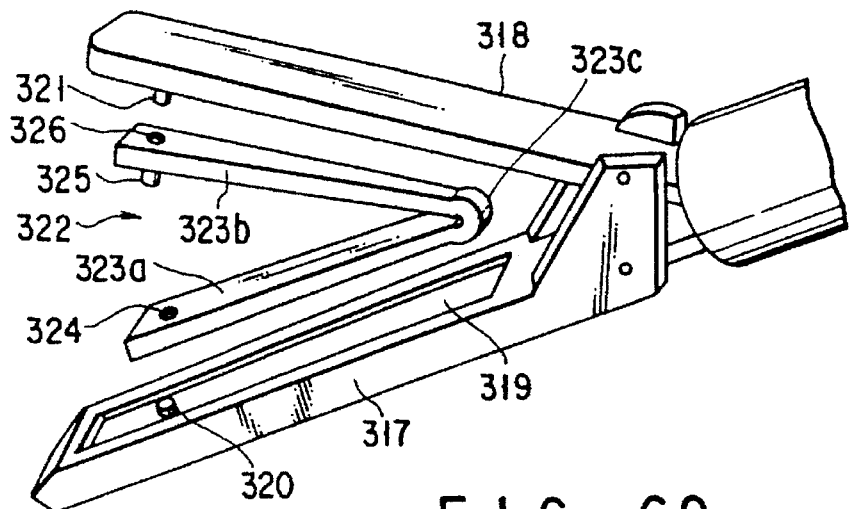
FIG. 69 is a perspective view illustrating the jaw of a clip applicator which is a twenty-third embodiment of this invention.
Figure 70:
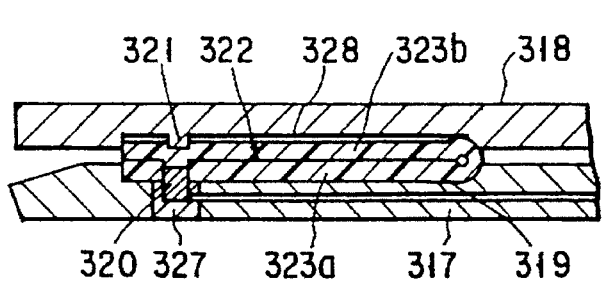
FIG. 70 is a sectional view showing the jaw of FIG. 69.

A twenty-third embodiment of the invention will be described with reference to FIGS. 69 and 70. FIG. 69 shows the distal end portion of a clip applicator according to this embodiment. As FIG. 69 shows, the applicator has a pair of jaws 317 and 318. The first jaw 317 has a clip-holding groove 319 formed in its inner surface and a rod-shaped heater 320 protruding from the bottom of the clip-holding groove 319. As is shown in FIG. 70, the heater 320 is held by an heat-insulating member 327 which is embedded in the first jaw 317. The second jaw 318 has a clip-holding groove 328 and a clip-holding projection 321 protruding from the bottom of the groove 328.

The jaws 317 and 318 are designed to close a clip 322. The clip 322 comprises a pair of legs 323a and 323b and a hinge 323a connecting the legs 323a and 323b at one end. All components of the clip 310 are formed integral and made of thermoplastic resin. The leg 323a has a through hole 324 in its free end portion, whereas the leg 323b has a projection 325 protruding from the inner surface of its end portion. The projection 325 is so positioned as to fit into the hole 324 of the leg 323a when the clip 322 is closed. The leg 323b has a hole 326 in the outer side of its end portion, for receiving the clip-holding projection 321 of the second jaw 318.

To load the clip 322 in the distal end portion of the clip applicator, the leg 323a is placed in the clip-holding groove 319 of the first jaw 317, and simultaneously the rod-shaped heater 320 is inserted into the hole 324 of the leg 323a. Further, the leg 323b is placed in the clip-holding groove 328 of the second jaw 318, and the clip-holding projection 321 of the second jaw 318 is inserted into the hole 326 of the leg 323b. As a result, the clip 322 is held between the jaws 317 and 318, in its open position.

The distal end portion of the clip applicator is guided into a body cavity and moved until the body tissues to be fastened together are caught in the gap between the legs 323a and 323b. Thereafter, the heater 320 is turned on, heating the projection 325 of the leg 232b and fusing the same to the leg 323a. The legs 323a and 353b are thereby permanently fastened to each other, clamping the tissues between them steadfastly.

It is only the projection 325 that the heater 320 heats. Since no other parts of the clip 322 are heated very little or not heated at all, the tissues are not thermally affected. The rod-shaped heater 320 may be replaced by a stylus-shaped one, so that the projection 325 may be heated more efficiently.

Figure 71:
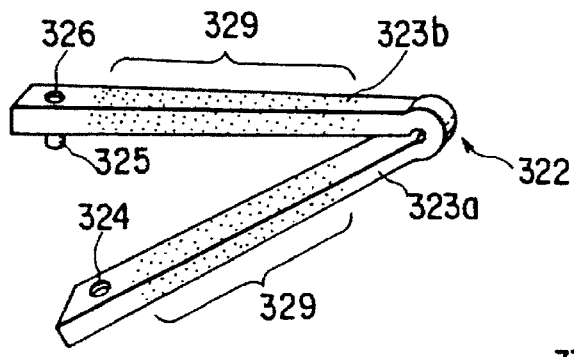
FIG. 71 is a perspective view showing a clip which is a twenty-fourth embodiment of the present invention.
Figure 73:
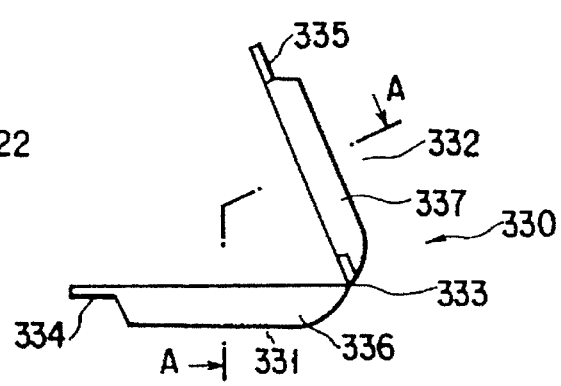
FIG. 73 is a side view of the clip illustrated in FIG. 72.

FIG. 71 shows a clip which is a twenty-fourth embodiment of the present invention. This clip is identical to the clip 322 shown in FIG. 69, except that a heat-sensitive material, which changes color as it is heated, is contained in the middle portions 329 of legs 323a and 323b. The clip is applied by the same method as the clip 322 of FIG. 69. Hence it is possible to detect the temperature to which the legs 323a and 323b have been heated, from the color the middle portions 329 do present. This helps to heat and fuse the projection 325 appropriately.

A clip 330, which is a twenty-fifth embodiment of the invention, will be described with reference to FIGS. 72, 73, 74A, 74B, and 75. The clip 330 is of a type which is permanently closed by means of ultrasonic oscillation.

Figure 72:
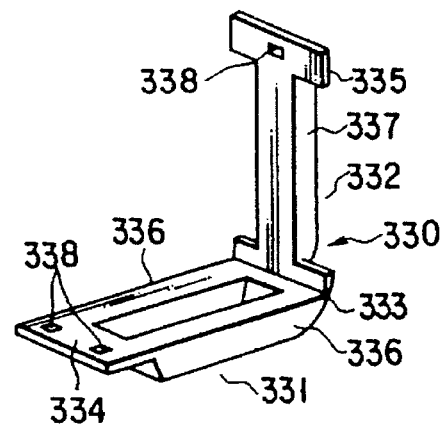
FIG. 72 is a perspective view illustrating a clip which is a twenty-fifth embodiment of the invention.
Figures 74A, 74B:
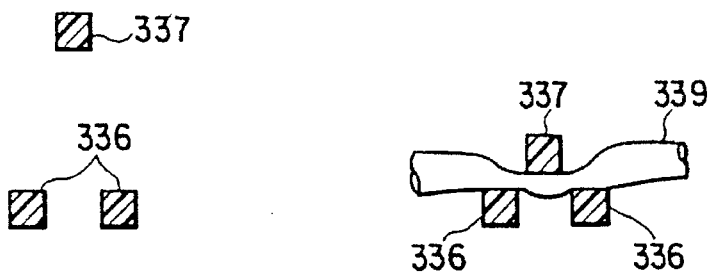
FIGS. 74A and 74B are cross-sectional views of the clip, taken along line A—A in FIG. 73.

As shown in FIG. 72, the clip 330 comprises a pair of legs 331 and 332 and a hinge 333 connecting the legs 331 and 332 at one end. All components of the clip 330 are formed integral and made of thermoplastic resin. The middle portions of the legs 331 and 332 function as tissue-clamping members. The legs 331 and 332 have thin plate-like end portions 334 and 335 which are to be fused together. The middle portion of the leg 331 is comprised of two parallel square bars 336, and that of the leg 332 is comprised of one square bar 337. These bars 336 and 337 are thicker than the end portions 334 and 335. The bars 336 are spaced apart for a distance slightly longer than the width of the bar 337. As long as the clip 330 remain open, the bars 336 and 337 assume such positions as shown in FIG. 74A. When the clip 330 is closed, the bar 337 will have its lower side substantially covering the space between the the bar 336, as is illustrated in FIG. 74B. The end portion 334 of the leg 331 has projections 338 on its inner surface. Similarly, the end portion 335 of the leg 332 has a projection 338 on its inner surface.

Figure 75:
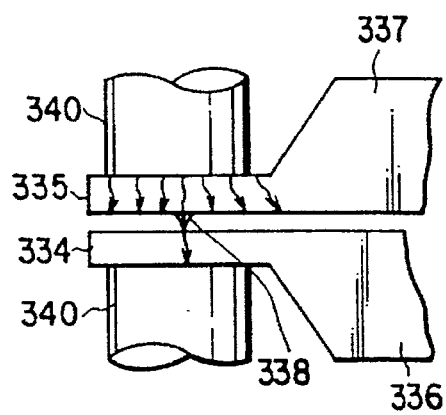
FIG. 75 is a diagram explaining how to fuse together the legs of the clip shown in FIG. 72.

The clip 330, thus constructed, is applied in the following way. The clip 330 is held in its open position, at the distal end of a clip applicator (not shown), which is guided into a body cavity. In the body cavity the distal end of the applicator is moved until a tubular organ 339 the clip 330 is to ligate is placed between the legs 331 and 332. Then, the clip 330 is closed, with the end portions 334 and 335 pressed together by the oscillating tips 340 of the applicator as is shown in FIG. 75. In this condition, the tips 340 applies ultrasonic oscillation to the end portions 334 and 335. The projections 338 of the end portion 334, which are in frictional contact with the end portion 335, and the projection 338 of the end portion 335, which is in frictional contact with the end portion 334, are heated and fused. Also, the end portion 334 and 335 are eventually fused together. As a result, the clip 330 firmly clamps the tubular organ 339.

Since the end portions 334 and 335 are thinner than the bars 336 and 337, the heat can hardly be transmitted to the bars 336 and 337 clamping the organ 339. Further, since the bars 336 and 337 do not contact one another, they have no friction among them and, hence, will generate no heat and will not fuse together. Hence, only the end portions 334 and 335 are fused together. Thus, the tubular organ 339 clamped by the bars will not be thermally affected at all.

Figure 76:
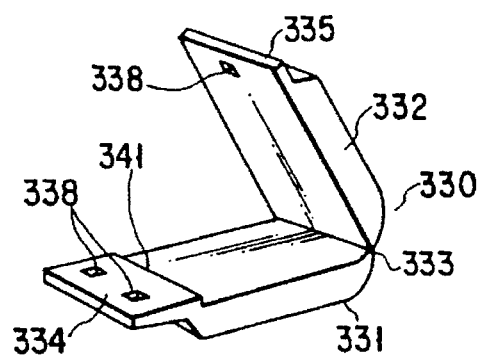
FIG. 76 is a perspective view showing a clip which is a twenty-sixth embodiment of the invention.

FIG. 76 shows a clip 330 which is a twenty-sixth embodiment of the present invention. The clip 330 comprises a pair of legs 331 and 332 and a hinge 333 coupling the legs 331 and 332. The middle portions of the clip 332 are flat plates, not bars as those of the clip shown in FIG. 72. The leg 331 has a step 341 in the inner surface, so that when the clip 330 is closed, the middle portion of the leg 331 does not touch the leg 332 though the plate-like end portions 334 and 335 contact each other. The clip 330 of FIG. 76 is identical to the clip shown in FIG. 72 (i.e., the twenty-fifth embodiment) in function and advantage. Body tissues or organs clamped by the clip 330 are not thermally affected only if the end portions 334 and 335 are thin or only if the middle portions of the legs 331 and 332 do not contact.

Figure 77:
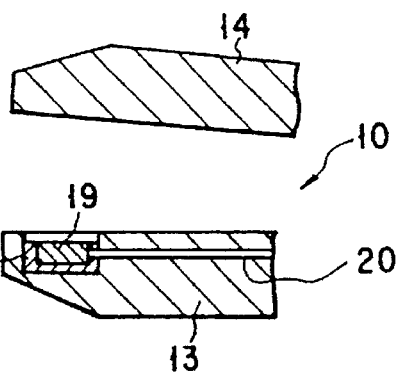
FIG. 77 is a sectional view showing the jaws of a clip applicator according to a twenty-seventh embodiment of the present invention.

FIG. 77 shows a clip applicator 10 according to a twenty-seventh embodiment of this invention, which is a modification of the first embodiment (FIG. 1). The applicator 10 is characterized in that the electric heater 19 attached to the first clip-holding member 13 is wrapped by a heat-insulating member 345. The heat-insulating member 345 can be made of various materials such as ceramic, gas- or liquid-sealed material, or heat-resistant resin (e.g., fluorine resin). It is only the pin 4 of the clip that contacts the electric heater 19. Therefore, the heat the heater 19 generates is not transmitted to any other component of the clip, and the heat is applied concentratedly to the pin 4.

Another clip applicator, which is a twenty-eighth embodiment of the invention, will be described with reference to FIGS. 78 and 79.

Figure 78:
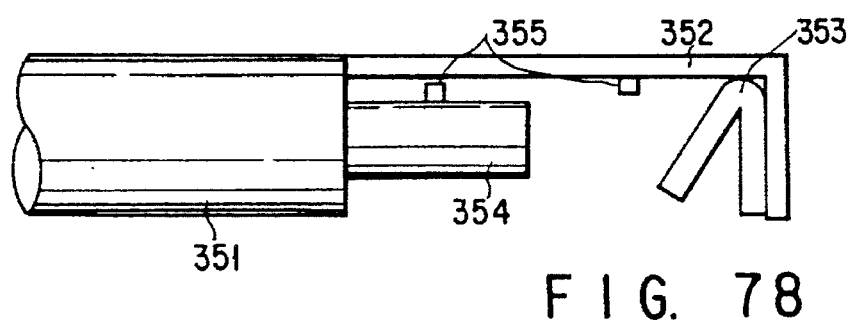
FIGS. 78 and 79 are perspective views illustrating a clip applicator according to a twenty-eighth embodiment of the invention.
Figure 79:
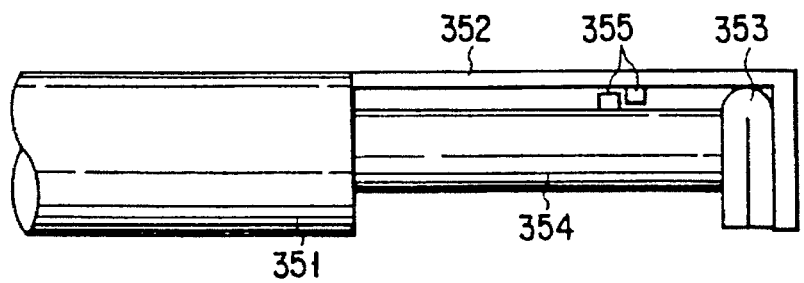

As can be understood from FIGS. 78 and 79, the applicator comprises a sheath 351, a clip holder 352 extending through the sheath 351 and protruding from the distal end thereof, and a rod-shaped oscillation-transmitting member 354 extending through the sheath 351 and protruding there of. The clip holder 352 has an tip which is L-shaped to hold a clip 353. The member 354 is connected at its proximal end to an ultrasonic oscillator (not shown) which is housed in the proximal end of the applicator. The member 354 can be moved back and forth, for transmitting ultrasonic oscillation generated by the oscillator to the clip 353 held at the tip of the holder 352. When pushed forward, the oscillation-transmitting member 354 can press the clip 353 firmly onto the tip of the clip holder 352 and can apply ultrasonic oscillation to the clip 352.

Two stoppers 335 protrude from the clip holder 352 and the oscillation-transmitting member 354, respectively. The stopper 335 on the member 354 abuts on the stopper 335 on the clip holder 352, upon moving toward the tip of the holder 352 for a predetermined distance, preventing any further forward motion of the member 354.

The clip applicator applies the clip 353 in the following way. First, the distal end of the applicator is inserted into a body cavity, with the clip 353 held at the tip of the clip holder 352. The distal end of the applicator is moved in the body cavity, thereby placing a tubular organ (not shown) such as a blood vessel in the gap between the legs of the open clip 353. Then, the oscillation-transmitting member 354 is pushed forward, closing the clip 353, which clamps the tubular organ. The ultrasonic oscillator is driven, generating ultrasonic oscillation. The member 354 transmits the oscillation to the clip 353, whereby the legs of the clip 353 are fused to each other at their contacting surfaces, ligating the tubular organ.

When the stopper 355 on the member 354 abuts on the stopper 355 on the clip holder 352, the member 354 can no longer move forward and ceases to contact the clip 353. Hence, the ultrasonic oscillation is no longer applied to the clip 353, and the legs of the clip 353 are not fused further. The tubular organ is, therefore, clipped steadfastly.

Figure 80A:
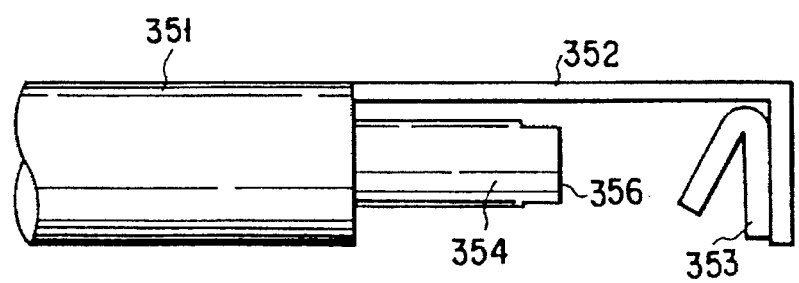
FIG. 80A is a perspective view showing the distal end portion of a clip applicator according to a twenty-ninth embodiment of this invention.
Figure 80B:
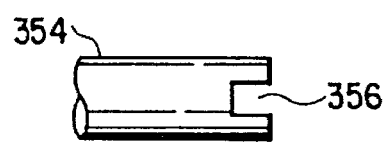
FIG. 80B is a plan view showing the distal end portion of the oscillation-transmitting member of the applicator shown in FIG. 80A.
Figure 81:
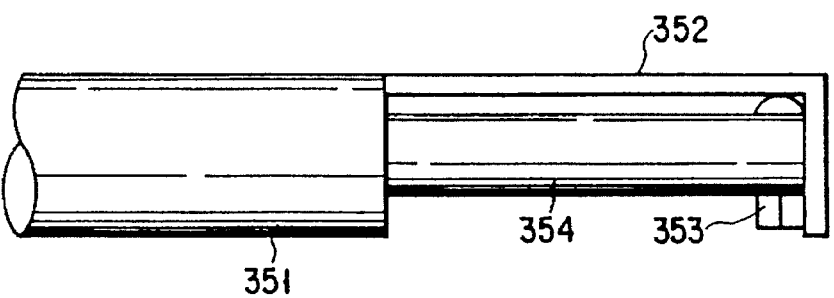
FIG. 81 is a side view showing the distal end portion of the clip applicator shown in FIG. 80A.
Figure 82:
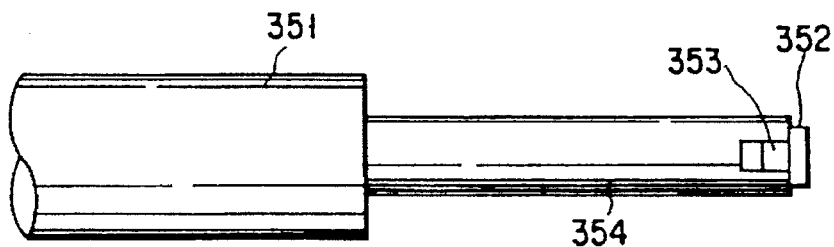
FIG. 82 is a plan view illustrating the distal end portion of the clip applicator shown in FIG. 80A.

A clip applicator according to a twenty-ninth embodiment of the invention will be described, with reference to FIGS. 80A, 80B, 81, and 82. The applicator differs from the twenty-eighth embodiment (FIG. 78 and 79) in two respects. First, neither the clip holder 352 nor the oscillation-transmitting member 354 has a stopper. Second, the member 354 has a groove 356 cut in its distal-end face, as is illustrated in FIGS. 80A and 80B. The groove 356 serves the purpose of holding the clip 353 steadily.

The clip applicator is used in the following way, in order to ligate a tubular organ (e.g., a blood vessel). One of the legs of the clip 353 is fitted in the groove 356 cut in the distal-end face of the oscillation-transmitting member 354. This done, the distal end of the applicator is inserted into a body cavity and moved therein, thereby placing the tubular organ between the legs of the clip 353. Thereafter, the member 354 is thrust toward the tip of the clip holder 352, thereby collapsing or closing the clip 353. The clip 353 clamps the tubular organ such as a blood vessel. In this condition, the ultrasonic oscillator is driven, generating ultrasonic oscillation. The member 354 transmits and applies the oscillator to the clip 353. As a result, heat is generated at those surfaces of the clip legs which are in frictional contact, whereby the legs of the clip 353 fuse to each other. The moment the member 354 abuts on the tip of the clip holder 352, it can no longer apply the ultrasonic oscillation to the clip 353, because the groove 356 is slightly deeper than the thickness of the clip 353 completely closed.

Hence, the clip 353 are not fused further. The tubular organ is, therefore, clipped reliably.

Figure 83:
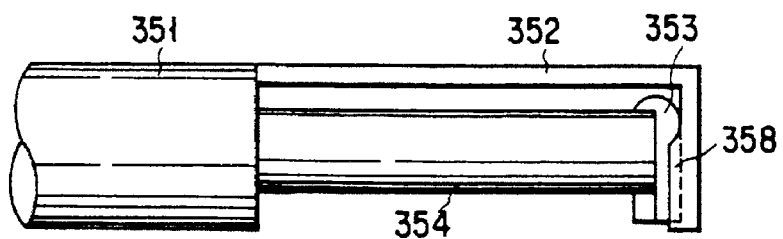
FIGS. 83 and 84 are a side view and plan view of a clip applicator which is a thirtieth embodiment of the present invention.
Figure 84:
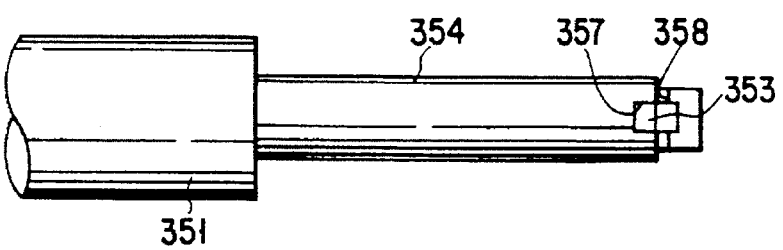

A clip applicator according to a thirtieth embodiment of the invention will be described, with reference to FIGS. 83 and 84. This applicator differs from the twenty-eighth embodiment (FIGS. 78 and 79) in three respects. First, neither the clip holder 352 nor the oscillation-transmitting member 354 has a stopper. Second, the member 354 has a groove 357 cut in its distal-end face, for receiving the clip 353 held at the tip of the clip holder 352. Third, the tip of the clip holder 352 has a groove 358 for receiving the clip 353.

Figure 85:
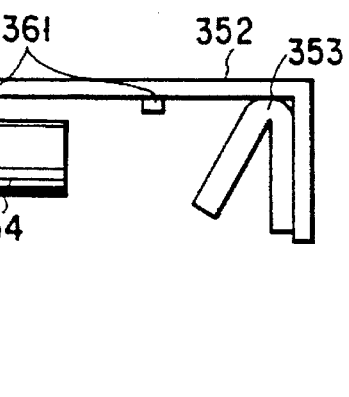
FIG. 85 is a schematic representation of a clip applicator according to a thirty-first embodiment of the present invention.

A clip applicator, which is a thirty-first embodiment of the invention, will be described with reference to FIG. 85. The clip applicator is identical to the twenty-eighth embodiment (FIG. 78 and 79), except that the stopper on the clip holder 352 and the stopper on the oscillation-transmitting member 354 are used as switch contacts 361 for driving a drive circuit 362 which is connected to an ultrasonic oscillator (not shown). The clip applicator is manipulated in the same way as the clip applicator shown in FIGS. 78 and 79, placing a tubular organ such as a blood vessel in the gap between the legs of the clip 353. Then, the member 354 is moved forward, closing the clip 353 held at the tip of the clip holder 352. The clip 353 thereby clamps the tubular organ. Thereafter, the ultrasonic oscillator is turned on, generating ultrasonic oscillation. The member 354 applies the oscillation to the clip 353. As a result, heat is generated at those surfaces of the clip legs which are in frictional contact, and the legs of the clip 353 fuse to each other. Then, the switch contact 361 on the the member 354 abuts on the switch contact 361 on the clip holder 352, whereupon the drive circuit 362 stops supplying drive signals to the ultrasonic oscillator. Subsequently, the oscillator cease to generate ultrasonic oscillation. Hence, the clip 353 are not fused further. The tubular organ, e.g., a blood vessel, is therefore clipped reliably.

Figure 86:
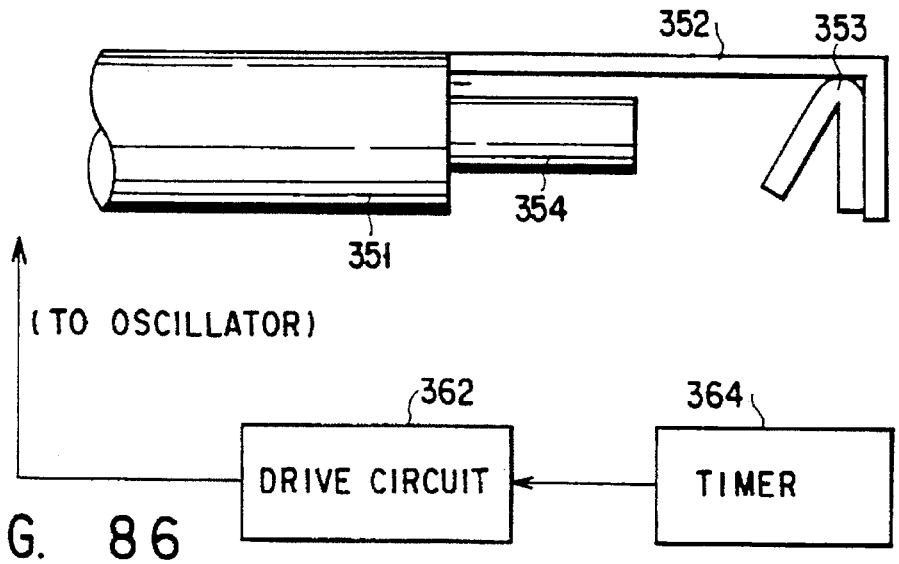
FIG. 86 is a diagram schematically showing a clip applicator which is a thirty-second embodiment of this invention.

A clip applicator, which is a thirty-second embodiment of the invention, will be described with reference to FIG. 86. This clip applicator is a modification of the thirty-first embodiment (FIG. 85), and is different in that a timer 364 is used in place of the switch contacts 361. The timer 364 is connected to a drive circuit 362 for driving an ultrasonic oscillator (not shown). The time the legs of the clip 353 require to fuse completely to each other, while being oscillated is set in the timer 364. Hence, upon lapse of this period, or the moment the legs of the clip 353 are completely fused together, the timer 364 supplies a stop signal to the drive circuit 362. In response to the stop signal the drive circuit 362 stops supplying drive signals to the ultrasonic oscillator, which ceases to generate ultrasonic oscillation. Hence, the fusion of the legs of the clip 353 automatically is terminated. Thus, the clip 353 can firmly clamp a tubular organ such as a blood vessel.

A clip applicator, which is a thirty-third embodiment of this invention, will be described with reference to FIG. 87. This clip applicator is a modification of the thirty-second embodiment (FIG. 86), and is characterized in that a temperature sensor 365 is used in place of the timer 364. The sensor 365 is connected to a drive circuit 362 for driving an ultrasonic oscillator (not shown). The temperature sensor 365 is embedded in the clip-holding side of the tip of the clip holder 352, so as to detect the temperature of the clip 353 held at the tip upon detecting that the temperature of the clip 353 has reached a predetermined value, indicating that the legs of the clip 353 have Just fused together, the sensor 365 outputs a signal to the drive circuit 362. In response to this signal the circuit 362 stops supplying drive signals to the ultrasonic oscillator, which ceases to generate ultrasonic oscillation. Hence, the legs of the clip 353 will not fuse excessively.

A clip 370, which is a thirty-fourth embodiment of the present invention, will be described with reference to FIGS. 88A and 88B and FIGS. 89A and 89B.

The clip 370 is a one-piece member made of thermoplastic resin. As shown in FIGS. 88A and 88B, the clip 370 comprises a pair of legs 371a 371b and a hinge 372 connecting the legs 371a and 371b together. Each leg consists of a tissue-holding portion 373 and a fusing portion 374. The fusing portion 374 has a fusing surface 375. As can be understood from FIGS. 89A and 98B, the fusing surfaces 374 of the legs 371a and 371b will contact when the clip 370 is closed as the legs 371a and 371b are rotated in a plane parallel to their fusing surfaces 374.

The clip 370 is applied in the following way. A tubular organ such as a blood vessel is positioned between the legs 371a and 371b, and the clip 370 is closed as shown in FIG. 89A. An clip applicator (not shown) is manipulated, applying forces to the closed clip 370 in the directions of arrows as illustrated in FIG. 89B, while the fusing portions 374 are being heated by means of a heater or ultrasonic oscillation. As a result, the portions 374 are fused together at their fusing surfaces 375.

The organ clamped between the legs 271a and 271b may have elasticity great enough to apply forces to push the clip 270 open and, hence, to apply shearing force at the fusing surfaces 375 of the fusing portions 374. Nonetheless, the mutual fusion of the portions 374 is so strong that the clip 370 remains closed, clamping the tubular organ firmly and steadily.

FIGS. 90 and 91 shows a clip which is a thirty-fifth embodiment of this invention. This clip is also a one-piece clip made of thermoplastic resin. As shown in FIG. 90, the clip comprises a pair of legs 376a 376b and a hinge 377 coupling the legs 376a and 376b together. The leg 376b has a wedge-shaped projection 378 protruding from the inner surface of its free-end portion. The other leg 376b has a recess 379 formed in the inner surface of its free-end portion. The projection 378 and the recess 379 serve as means for preventing the legs 376a and 376b from moving relative to each other.

When the clip is closed as is illustrated in FIG. 91, the projection 378 of the leg 376b is fitted into the recess 379 of the leg 376a. The sides of the projection 378 contact the sides of the recess 379. These sides are substantially parallel to the plane in which the legs 376a and 376b are rotated. The organ (not shown) clamped between the legs 276a and 276b may have elasticity great enough to apply forces to push the clip open and, hence, to apply shearing force at the contacting sides of the projection 378 and the recess 379. Nonetheless, the projection 378 remains fitted in the recess 379 since the projection 378, which is wedged-shaped, has tightly fitted into the recess 379 having a cross section complementary to that of the projection 378.

After the clip has been closed, the distal end portions of the legs 376a and 376b are pinched together by applying forces in the directions of arrows, as illustrated in FIG. 91, while the free-end portions of the legs 376a and 376b are being heated, by means of a heater or ultrasonic oscillation, at the contacting sides of the projection 378 and the recess 379. As a result, the free-portions 374 are fused together, clamping a tubular organ (not shown) such as a blood vessel steadfastly.

FIGS. 92 and 93 shows a clip 380 which is a thirty-sixth embodiment of this invention. The clip 380 is a one-piece clip made of thermoplastic resin. As shown in FIG. 92, the clip 380 comprises a pair of legs 381a 381b and a hinge 382 coupling the legs 381a and 381b together. The leg 381b has a fusing tongue 383 extending downwards from its free end. The tongue 383 contacts the end face of the leg 381a when the clip 380 is closed, as is illustrated in FIG. 93. The connecting surfaces of the tongue 383 and the leg 381a is perpendicular to the plane in which the legs 381a and 381b are rotated.

The clip 380 is applied as follows to clamping a tubular organ such as a blood vessel. First, the clip 380 in its open state is moved such that the organ is placed in the gap between the legs 381a and 381b. This done, the clip 380 is closed, and the free-end portions of the legs 381a and 381b are heated by means of a heater or ultrasonic oscillation and thereby fused together at the contacting surface of the tongue 383 and the free end of the leg 381a. The organ (not shown) clamped between the legs 276a and 276b may have elasticity great enough to apply forces to push the clip 380 open and, hence, to apply shearing force at the contacting surfaces of the tongue 383 and the free end of the leg 381a. In spite of the shearing force, the tongue 383 remains fused to the end face of the leg 381a. As a result, the clip 380 keeps clamping the tubular organ between its legs 381a and 381b.

A clip applicator 405, which is a thirty-seventh embodiment of the invention, will be described with reference to FIGS. 94 to 96.

FIG. 94 shows a clip 401 which the applicator 405 (FIG. 95) is to apply. The clip 401 comprises a pair of legs 403 and a hinge 402 connecting the legs 403. Each leg 403 has a projection 404 protruding from its outer surface. Either the hinge 402 or the entire clip 401 may be heated to be permanently deformed to clamp body tissues between the legs 403.

The clip 401 is made of a polymer or copolymer of dioxanone, lactide or glycolide. Of the polymer, 5 to 50% by weight is monomer having a relatively low molecular weight of 10,000 or less. Hence, the polymer has a thermal-deforming point of 100° C., more preferably 45° to 80° C.

As shown in FIG. 95, the clip applicator 405 comprises an insertion section 406 which is a thin pipe. A pair of clip-holding members 408 and 409 are rotatably connected at one end by a hinge 407, thus constituting a clip holder. The first clip-holding member 408 is fastened to the distal end of the insertion section 406. Each clip-holding member has a groove 410 in its inner surface. The grooves 410 of the members 408 and 409 are positioned to face each other. The grooves 410 will receive the projections 404 of the clip 402 when the member 409 is rotated into its closed position, with the clip 401 held between it and the member 408.

A pin 411 protrudes sideways from the distal end portion of the clip-holding member 409. A connector 412 is rotatably connected at one end to the pin 411. The other end of the connector 412 is fastened to the distal end of an operating rod 413, which extends through the insertion section 406. The rod 413 protrudes from the proximal end of the section 406. Fixed to the proximal end of the insertion section 406 is an operating handle 417. The handle 417 comprises a handle 414 fixed to the proximal end of the insertion section 406, a handle 416 rotatably connected to the fixed handle 414 by a pin 415. The upper end of the notable handle 416 is connected to the proximal end of the operating rod 413. Hence, when the handle 416 is moved toward and away from the fixed handle 414, the rod 413 is pulled backward and forward, opening and closing the clip holder constituted by the members 408 and 409.

The insertion section 406 has a fluid passage 418. The passage 418 extends between the distal opening 419 of the insertion section 406 and a connecting tube 420 protruding from the proximal end portion of the section 406. A syringe 421 is removably coupled to the connecting tube 420.

The clip applicator 405 is manipulated as follows to apply the grip 410 in order to ligate a tubular organ such as a blood vessel and a bile duct.

First, the rotatable handle 416 is moved, thereby rotating the clip-holding member 409 into the open position as shown in FIG. 96. The clip 401 is put into the gap between the clip-holding members 408 and 409. Once the projections 404 of both clip legs 403 enter the grooves 410 of the members 408 and 409, the clip 401 can hardly slip out of the nip between the clip-holding members 408 and 409.

Then, the insertion section 406 is inserted into the body cavity where a tubular organ 422 to ligate is located. The section 406 is further moved, thereby catching the organ 422 between the legs 403 of the clip 401. Next, the rotatable handle 417 is squeezed, pushing the operating rod 413 forward. The clip-holding member 409 is thereby rotated into the closed position, closing the clip 401 and, hence, collapsing the tubular organ 422.

In this condition, the piston of the syringe 421 connected to the fluid passage 418 is pushed, pumping a heated fluid to the distal opening 419 of the insertion section 406 through the fluid passage 418. The heated fluid is hence applied onto the clip 401. The fluid is hot enough to deform the clip 401 thermally. Heated with the fluid, the clip 401 softens such that the legs 403 wraps the tubular organ 422 as is shown in FIG. 97. Thereafter, the piston of the syringe 421 is pushed, this time, pumping cold water to the distal opening 419 of the insertion section 406 through the fluid passage 418 and subsequently applying the cold water onto the clip 401. The fluid is hot enough to deform the clip 401 thermally. Cooled with the water, the clip 401 hardens and is permanently deformed, thus clamping the tubular organ 422 steadfastly.

Merely by thermally deformed with the heated fluid, the clip 401 can reliably ligate the tubular organ 422—requiring no mechanical fastening means whatever. Therefore, the clip 401 can be made small and simple. In addition, the clip 401 can be softened at a relatively low temperature, hot water and cold water can sell serve as heating medium and cooling medium, respectively.

A clip applicator 405, which is a thirty-eighth embodiment of the invention, will be described with reference to FIG. 98. The clip applicator 405 is identical to the thirty-seventh embodiment (FIG. 95), except in that heater 424 such as a diode or a ceramic heater is set in a recess 423 made in the inner surface of the clip-holding member 405. The heater 424 is electrically connected by to a power supply (not shown) provided outside the applicator 405 by a lead wire 425 which extends through the insertion section 406 and out of the proximal end of the section 406.

After the clip-holding member 409 is rotated into its closed position, thus closing the clip 401 and ultimately collapsing the tubular organ 422 held between the members 408 and 408 of the clip 401, an electric current is supplied from the power supply via the lead wire 425 to the heater 424. The heater 424 generates heat, which thermally deforms the clip 401. Then, both legs 403 of the clip 401 are cooled and permanently deformed, firmly clamping the organ 422 between them.

The clip heating/cooling means is not limited to those employed in the thirty-seventh embodiment (FIG. 95) and the thirty-eighth embodiment (FIG. 98). Instead, a laser beam or hot air may be utilized as clip-heating medium, and any coolant other than cold water (e.g., coolant gas) may be used as clip-cooling medium.

A staple 431, which is a thirty-ninth embodiment of this invention will, will be described with reference to FIGS. 99 and 100. As is shown in FIG. 99, the staple 431 (used as a suture) is a strip having two clawed ends 432, each extending downwards from one end. The staple 431 has two grooved portions 433 having a groove made in its upper surface, at a ⅓-length distance from the ends, respectively.

The staple 431 is made, as a whole, of polymer or copolymer of dioxanone, lactide or glycolide. The polymer or copolymer contains 5 to 40% by weight of a platicizer, either fatty acid or ester of fatty acid, and thus has a thermal-deforming point of 45° to 80° C. Various commercial available plasticizers can be used in the polymer or copolymer, but preferable for use in the invention are: dibutyl sebacate, epoxidated soybean oil, dibutyl stearate, epoxidated safflower oil, esters of oleic acid, and esters of linoleic acid.

The staple 431 is applied in the following way to stitch body tissues together. First, the staple 431 is heated and softened. Then, one clawed end 433 of the staple 431 is forced into the end portion of a tissue 434a, piercing the same, as shown in FIG. 100. Further, the staple 431 is bent at the first grooved portion 433. The staple 431 is then bent at the grooved portion 433, and other clawed 433 of the staple 431 is then forced into the end portion of a tissue 434b, piercing the same. As a result, the staple 431 is deformed as illustrated in FIG. 100. Finally, the staple 431, thus deformed thermally, is cooled and hardened, firmly stitching the body tissues 434a and 434b to each other.

The staple 431 may be heated, deformed, and hardened by means of either a special-purpose stapler or by a general-purpose stapler.

Merely by thermally softened, then deformed, and finally cooled and permanently deformed, the staple 431 can suture body tissues 434a and 434b together, both readily and reliably—requiring no mechanical fastening means whatever. The staple 431 can therefore be made small and simple. Moreover, the staple 431 can be softened at a relatively low temperature, it can be heated and cooled by a comparatively simple method.

FIG. 101 shows a clip 435 which is a fortieth embodiment of the present invention. The clip 435, which is identical in shape to the clip 401 (FIG. 94), is made of polymer or copolymer of dioxanone, lactide or glycolide. The polymer or copolymer contains 5 to 40% by weight of an oily image intensifier such as Urographine (tradename) or Lipodole (trade name), and thereby has a thermal-deforming point of 45° to 80° C.

The clip 435 is applied in the same way as the clip 401 (FIG. 94). The clip 435 achieves the same advantage as the clip 401. It also attain additional advantages. First, since the clip 435 is made of polymer or copolymer containing an image intensifier, its position in an patient can be determined by means of X-ray photography. Second, as the clip 435 is absorbed into a body organ, so is the image intensifier, making it possible to determine how much the clip 435 has been absorbed into the organ merely by tracing the image intensifier in an X-ray photograph of the clipped organ.

FIG. 102 shows a clip 436 which is a forty-first embodiment of the present invention. This clip 426 has the same strength as the clip 435 but is smaller and thinner. Resin which can be absorbed into body tissues has but a small mechanical strength. A clip or staple made of such resin must inevitably made large and thick to have a sufficient strength. To be adequately strong, the clip 435 is made of polymer or copolymer of dioxanone, lactide or glycolide, which contains powders of one or two ceramics absorbable into body tissues, selected from the group consisting of tricalcium phosphate (TCP), hydroxyapatite (HAP), and tetracalcium phosphate—in total amount of 5 to 45% by weight.

Made of polymer or copolymer containing ceramic powders, the clip 436 can have sufficient strength though it is small and thin. Since the ceramic powder contained in the polymer or copolymer is also absorbable into body tissues, the clip 436 will be absorbed in its entirety into the body tissues to which it has been applied.

The material absorbable into body tissues, which is used in the invention, may be one hitherto used or one having a low thermal-deforming point. Even if the glass ceramic powder is absorbed into body tissues at so slow a rate as to remain unabsorbed into the tissuesm, it will not affect the body tissues at all.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A surgical instrument for fastening together adjacent portions of a body tissue, comprising:
    a staple having first support means for supporting one of the adjacent portions of the body tissue, second support means for supporting the other of the adjacent portions of the body tissue, and connecting means having a proximal end portion fastened to said first support means and a distal end portion, at least said distal end portion becoming soft when heated and fastened to said second support means when hardened after having been softened; and
    an applicator having operation means for provisionally holding said first and second support means, for positioning said first support means at one of said adjacent portions of the body tissue, for positioning said second support means at the other of said adjacent portions and for causing said first and second support means to clamp the body tissue, thereby to align said distal end portion with said connecting means, and a heater for heating and softening the distal end portion of said connecting means, thereby to fastening the distal end portion of the connecting means to said second support means.

2. The surgical instrument according to claim 1, wherein said staple is made of thermoplastic resin which is absorbable into the body tissue.

3. The surgical instrument according to claim 1 wherein at least of said first and second support means has a net-like member.

4. The surgical instrument according to claim 1, wherein said fist support means has a net-like member, and the proximal end portion of said connecting has a head portion to be fastened to said net-like member.

5. The surgical instrument according to claim 1, wherein said second support means has a net-like member, and the distal end portion of said connecting means is inserted into the net-like member when aligned with positioned at the net-like member.

6. The surgical instrument according to claim 1, wherein said heater is movable.

7. The surgical instrument according to claim 1, wherein said first and second support means are arranged in a circle and oppose each other.

8. The surgical instrument according to claim 1, wherein said second support means has a ring into which said connecting means is to be fitted.

9. The surgical instrument according to claim 1, wherein said first and second support means are two surfaces of a band-like member, respectively, which is wound around a tubular organ.

10. The surgical instrument according to claim 1, wherein said heater has an ultrasonic oscillator for applying ultrasonic vibration to the distal end portion of said connecting means, thereby to heat the distal end portion of said connecting means.

11. The surgical instrument according to claim 1, wherein said heater has a laser probe for applying a laser beam to the distal end portion of said connecting means, thereby to heat the distal end portion of said connecting means.

12. The surgical instrument according to claim 1, which further comprises further comprises another staple having first support means for supporting one of other two adjacent portions of the body tissue, second support means for supporting the other of the other two adjacent portions of the body tissue, and connecting means having a proximal end portion fastened to said first support means and a distal end portion, at least said distal end portion becoming soft when heated and fastened to said second support means when hardened after having been softened, and in which said applicator has knife means for cutting another portion of said body tissue, which connects the adjacent portions of said body tissue.

13. A staple for fastening together adjacent portions of a body tissue, comprising:
    a first claw provided at one end of said staple body, for piercing into one of the adjacent portions of the body tissue;
    a second claw provided at the other end of said staple body, for piercing into the other of the adjacent portions of the body tissue; and
    means provided on said staple body and capable of being deformed when heated and being hardened when cooled.

14. The surgical instrument according to claim 13, wherein said staple is made of thermoplastic resin which is absorbable into the body tissue.

15. A method of applying a staple to body tissues by means of an applicator, comprising the steps of:
    preparing a staple having legs made of thermoplastic resin and designed to pierce through the body tissues;
    loading the staple in said applicator;
    piercing the legs of said staple through the body tissue; and
    heating and deforming the legs of said staple and leaving the legs to cool, thereby to fasten the staple to the body tissues.

16. The method according to claim 15, wherein said thermoplastic resin is absorbable into the body tissues.

17. The method according to claim 16, wherein said thermoplastic resin is compatible with the body tissues.

18. A method of applying a staple to a body tissue, thereby to fasten two adjacent portions of the body tissue, comprising the steps of:
    preparing a staple comprising first support means having legs made of thermoplastic resin and designed to pierce into the body tissues, for supporting one of the adjacent portions of the body tissue, second support means for supporting the other of the adjacent portions of the body tissue;

loading the staple in an applicator;

piercing the legs of said first support means through the one of the adjacent portions of the body tissue;

connecting the legs of said first support means to said second support means; and heating and deforming the legs of the first support means, thereby securing the legs to the second support means, and leaving the legs to cool, thereby to fasten the first and second support means to the body tissue.

19. The method according to claim 18, wherein said first and second support means are made of thermoplastic resin which is absorbable into the body tissue.

20. The method according to claim 18, wherein said first and second support means are made of thermoplastic resin which is compatible with the body tissue.

21. A surgical instrument for fastening together adjacent portions of a body tissue, comprising:

a staple having a piercing portion to pierce through the body tissue, a holding portion for holding the body tissue, and a deformable portion which is sharp enough to pierce through the body tissue and which is capable of being softened when supplied with energy and of being deformed; and an applicator having operation means for causing the holding portion of said staple to hold the body tissue, and energy-supplying means for supplying energy to the deformable portion of said staple.

22. The surgical instrument according to claim 21, wherein the deformable portion of said staple is softened when supplied with ultrasonic waves and is deformed.

23. The surgical instrument according to claim 21, wherein the deformable portion of said staple is softened when supplied with a laser beam and is deformed.

24. The surgical instrument according to claim 21, wherein the deformable portion of said staple is softened when supplied with heat from a heater and is deformed.

25. The surgical instrument according to claim 21, wherein the deformable portion of said staple is bent when softened.

26. The surgical instrument according to claim 21, wherein the deformable portion of said staple connects the piercing portion to the holding portion when softened.

27. The surgical instrument according to claim 21, wherein the deformable portion of said staple collapses when softened.

28. The surgical instrument according to claim 21, wherein the deformable portion of said staple is deformed to have a permanent shape when softened.

29. The surgical instrument according to claim 21, wherein said applicator has second operation means for holding said staple.

30. The surgical instrument according to claim 21, wherein said energy-supplying means comprises an ultrasonic oscillator and a rod for transmitting vibration from the ultrasonic oscillator to the deformable portion of said staple.

31. The surgical instrument according to claim 21, wherein said energy-supplying means has an optical fiber for transmitting a laser beam to the deformable portion of said staple.

32. The surgical instrument according to claim 21, wherein said energy-supplying means has a heater for supplying heat to the deformable portion of said staple.

33. A method of applying a staple to body tissues by means of an applicator, comprising the steps of:

preparing a staple having a piercing portion made of thermoplastic resin and designed to pierce through the body tissue, a holding portion for holding the body tissue, and a deformable portion which is sharp enough to pierce through the body tissue and which is capable of generating heat supplied with energy and of being permanently deformed;

loading the staple in said applicator;

driving the piercing portion of said staple through the body tissue;

heating the deformable portion of said staple, thereby softening and deforming the deformable portion, and leaving the deformable portion to cool, thereby to fasten the staple to the body tissue.

34. The method according to claim 33, wherein said staple is made of thermoplastic resin which is absorbable into the body tissue.

35. The method according to claim 34, wherein said staple is made of thermoplastic resin which is compatible with the body tissue.

36. A method of applying a staple to a body tissue, thereby to fasten two adjacent portions of the body tissue, comprising the steps of:

preparing a staple comprising first support means for supporting one of the adjacent portion of the body tissue, having a piercing portion which is made of thermoplastic resin and which is designed to pierce through the body tissue and a deformable portion which is sharp enough to pierce through the body tissue and which is capable of generating heat supplied with energy and of being permanently deformed, second support means for supporting the other of the adjacent portions of the body tissue;

loading the staple in an applicator;

piercing the piercing portion of said first support means through the one of the adjacent portions of the body tissue;

connecting the piercing portion of said first support means to said second support means; and heating and deforming the deformable portion of the first support means, thereby securing the first support means to the second support means, and leaving the deformable portion to cool, thereby to fasten the first and second support means to the body tissue.

* * * * *